(12) United States Patent
Lehari

(10) Patent No.: US 11,341,864 B2
(45) Date of Patent: *May 24, 2022

(54) WIRELESS METRIC CALCULATING AND FEEDBACK APPARATUS, SYSTEM, AND METHOD

(71) Applicant: TRITONWEAR INC., Toronto (CA)

(72) Inventor: Tristan Vincent Hulbert Lehari, Uxbridge (CA)

(73) Assignee: TRITONWEAR INC., Kitchener (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/715,830

(22) Filed: Dec. 16, 2019

(65) Prior Publication Data

US 2020/0118460 A1 Apr. 16, 2020

Related U.S. Application Data

(63) Continuation of application No. 15/306,644, filed as application No. PCT/CA2015/000275 on Apr. 29, 2015.

(Continued)

(51) Int. Cl.
*G09B 19/00* (2006.01)
*G09B 5/12* (2006.01)
(Continued)

(52) U.S. Cl.
CPC ...... *G09B 19/0038* (2013.01); *A61B 5/02416* (2013.01); *A61B 5/02438* (2013.01);
(Continued)

(58) Field of Classification Search
CPC .......................... G09B 19/0038; G09B 5/125
See application file for complete search history.

(56) References Cited

U.S. PATENT DOCUMENTS 5,685,722 A 11/1997 Taba
7,917,768 B2 3/2011 Kahn
(Continued)

FOREIGN PATENT DOCUMENTS

CN 103124542 A 5/2013
CN 104635598 A 5/2015
(Continued)

OTHER PUBLICATIONS

CNIPA Office Action for CN Application No. 201580028697.6, dated Feb. 27, 2019.

(Continued)

*Primary Examiner* — Eddy Saint-Vil
(74) *Attorney, Agent, or Firm* — Norton Rose Fulbright Canada LLP

(57) ABSTRACT

A wearable computing device that is secured or attached to a resilient strap, the resilient strap sized to fit around at least a part of a circumference of a human head. The device has a waterproof storage volume housing a plurality of sensors. The wearable computing device may calculate a plurality of swimming metrics based at least partly on data received from the at least one sensor. The wearable computing device may include a wireless communication subsystem secured to the resilient strap within the waterproof storage volume and may transmit at least one of the calculated plurality of swimming metrics to at least one computing device via the wireless communication subsystem. The wearable computing device may include at least one user output component and may present an indication of at least one of the calculated plurality of swimming metrics at the at least one user output component for communication to the user. The indication may be audio played in an ear piece connected to the strap, or may be visually displayed on a display in an eye goggle portion of the strap.

20 Claims, 16 Drawing Sheets

Related U.S. Application Data

(60) Provisional application No. 61/985,681, filed on Apr. 29, 2014.

(51) Int. Cl.

| | |
|---|---|
| *A61B 5/024* | (2006.01) |
| *H04B 1/3888* | (2015.01) |
| *G06N 20/00* | (2019.01) |
| *G06F 1/16* | (2006.01) |
| *A63B 71/06* | (2006.01) |
| *A63B 69/00* | (2006.01) |
| *A63B 33/00* | (2006.01) |
| *A63B 24/00* | (2006.01) |
| *A61B 5/11* | (2006.01) |
| *A61B 5/00* | (2006.01) |
| *H04B 1/3827* | (2015.01) |
| *H04B 1/38* | (2015.01) |

(52) U.S. Cl.
CPC .......... *A61B 5/1123* (2013.01); *A61B 5/6803* (2013.01); *A61B 5/6814* (2013.01); *A61B 5/6831* (2013.01); *A61B 5/742* (2013.01); *A61B 5/7405* (2013.01); *A63B 24/0062* (2013.01); *A63B 33/00* (2013.01); *A63B 33/002* (2013.01); *A63B 69/00* (2013.01); *A63B 71/0622* (2013.01); *G06F 1/163* (2013.01); *G06N 20/00* (2019.01); *G09B 5/125* (2013.01); *H04B 1/3888* (2013.01); *A61B 2503/10* (2013.01); *A63B 33/004* (2020.08); *A63B 2071/0625* (2013.01); *A63B 2071/0655* (2013.01); *A63B 2208/03* (2013.01); *A63B 2220/10* (2013.01); *A63B 2220/12* (2013.01); *A63B 2220/17* (2013.01); *A63B 2220/20* (2013.01); *A63B 2220/30* (2013.01); *A63B 2220/40* (2013.01); *A63B 2220/44* (2013.01); *A63B 2220/62* (2013.01); *A63B 2220/803* (2013.01); *A63B 2220/836* (2013.01); *A63B 2225/20* (2013.01); *A63B 2225/50* (2013.01); *A63B 2230/06* (2013.01); *A63B 2230/20* (2013.01); *A63B 2230/40* (2013.01); *A63B 2230/75* (2013.01); *H04B 2001/3866* (2013.01); *H04B 2001/3894* (2013.01)

(56) References Cited

U.S. PATENT DOCUMENTS

| | | | |
|---|---|---|---|
| 7,980,998 | B2 | 7/2011 | Shemesh et al. |
| 8,406,085 | B2 | 3/2013 | Sakita |
| 8,696,420 | B2 | 4/2014 | Mueller et al. |
| 9,216,341 | B2 | 12/2015 | Li |
| 2005/0186542 | A1 | 8/2005 | Roncalez et al. |
| 2008/0018532 | A1 | 1/2008 | Mackintosh |
| 2009/0239710 | A1 | 9/2009 | Shemesh |
| 2010/0030482 | A1 | 2/2010 | Li |
| 2010/0210975 | A1* | 8/2010 | Anthony, III ........ A61B 5/0002 600/595 |
| 2011/0153042 | A1 | 6/2011 | Burton et al. |
| 2012/0009553 | A1 | 1/2012 | Ben-Tal |
| 2012/0072165 | A1 | 3/2012 | Jallon |
| 2012/0156991 | A1 | 6/2012 | Burton et al. |
| 2013/0018494 | A1 | 1/2013 | Amini |
| 2013/0053190 | A1 | 2/2013 | Mettler |
| 2013/0187786 | A1 | 7/2013 | Dadlani et al. |
| 2013/0244211 | A1 | 9/2013 | Downing |
| 2013/0274040 | A1 | 10/2013 | Coza |
| 2014/0031703 | A1 | 1/2014 | Rayner |
| 2014/0099615 | A1 | 4/2014 | Sweeney et al. |
| 2014/0188638 | A1 | 7/2014 | Jones |
| 2014/0200116 | A1* | 7/2014 | Boutov ............. G09B 19/0038 482/55 |
| 2014/0212858 | A1 | 7/2014 | Lewin |
| 2014/0228649 | A1 | 8/2014 | Rayner |

FOREIGN PATENT DOCUMENTS

| | | |
|---|---|---|
| WO | 2003061779 A1 | 7/2003 |
| WO | 2008032315 A1 | 3/2008 |
| WO | 2010090867 A2 | 8/2010 |
| WO | 2015092533 A1 | 6/2015 |
| WO | 2015155069 A1 | 10/2015 |

OTHER PUBLICATIONS

EPO Search Report for EP Application No. 15785330.0, dated Jan. 8, 2018.
WIPO International Search Report and Written Opinion for PCT Application No. PCT/CA2015/000275.
SIPO first Office Action for Chinese Patent Application No. 201580028697.6, dated Apr. 27, 2018.
SIPO Office Action and Search Report for Chinese Patent Application No. 201580028697.6, dated Apr. 19, 2018.
IP Australia, Examination Report No. 1 for Australian Application No. 2015252691 dated Jan. 31, 2020.
CIPO, Examiner's Report for Canadian Patent Application No. 2,946,902 dated Jun. 11, 2021.
Canadian Intellectual Property Office; Examiner's Report dated Feb. 17, 2022, issued in respect of Canadian Patent Application No. 2,946,902, Applicant: Tritonwear Inc.

\* cited by examiner

WIRELESS METRIC CALCULATING AND FEEDBACK APPARATUS, SYSTEM, AND METHOD

FIELD

Embodiments described herein relate generally to wearable computing. Embodiments described herein further relate to systems and methods for determining and reporting athletic activity data.

BACKGROUND

The majority of race based sports involve one coach, multiple athletes, and multiple crucial performance metrics per athlete. This generally creates the inevitable situation where there are too many performance metrics and too many athletes for a coach to focus on simultaneously. This results in the coach focusing on few athletes at a time or only one or two metrics at a time, with all of the other information being lost. Not only does this limit the amount of real time action that the coach can perform during a workout, but it also removes any possibility of long term tracking of these performance metrics over the athletes season. Naturally, if the coach cannot even calculate all of the metrics, it is impossible for them to record them. Competitive swimming is one example of these sports.

Competitive swimming, whether it is in a pool or in open water, is a sport driven by numbers and statistics. Many people do not realize it, but coaches and swimmers are constantly counting or calculating metrics while they are training. Coaches on deck do their best to track metrics, calculate metrics and act on over a dozen metrics at different times while also watching each swimmer in turn to find general technique problems. This process of calculating metrics is very time consuming within the limited practice times and can be inaccurate when a large number of athletes are in the water. As recording metrics is generally not practical or even impossible, there is no way for a coach or athlete to accurately track their progress over the course of a season or to note negative trends as they arise.

If the coach wants a swimmer to change something mid-swim he/she has to catch the swimmer's attention either by waving or yelling, then the swimmer has to stop mid-swim to listen, and then start again.

Team swimmers are not the only ones faced with challenges. The casual lane swimmer, non-team triathlete, or anyone swimming on their own face these same issues of trying to keep track of these and other swimming metrics but do not have the luxury of having a coach to help keep track of this data and fix technical issues. On top of this, a solo swimmer faces the problem of general boredom while swimming without a team.

Existing devices are intrusive to the swimmer such as a wrist/ankle band or chest strap which are less than ideal in a sport where minimizing resistance in the water may be important and directly impacts performance as well as the swimmer's "feel" in the water. Other devices require user interaction using an array of buttons. This required physical interaction further impedes the swimmer's experience during their workout.

SUMMARY

In accordance with an aspect of embodiments described herein, there is provided a wearable computing device for wearing on a head of a user. The device has at least one connection for connecting to a resilient strap sized to fit around at least a part of a circumference of a human head. The device has a waterproof storage volume and at least one sensor within the waterproof storage volume. There is at least one data processor secured within the waterproof storage volume coupled to at least one user output component and wireless transceiver and coupled to at least one non-transitory computer readable medium. The medium contains processing instructions that when executed by the at least one data processor, cause the at least one data processor to transmit the sensor data received from the at least one sensor to an external device such as a hub 14 or computing device. The external device may use the sensor data to calculate a plurality of swimming metrics.

In accordance with an aspect of embodiments described herein, the at least one data processor calculates a plurality of swimming metrics based at least partly on the sensor data.

In accordance with an aspect of embodiments described herein, the wearable computing device has a wireless communication subsystem secured to the resilient strap within the waterproof storage volume, the at least one data processor coupled to the wireless communication subsystem. Processing instructions cause the at least one data processor to: transmit at least one of the calculated plurality of swimming metrics to at least one computing device via the wireless communication subsystem.

In accordance with an aspect of embodiments described herein, the wearable computing device has at least one user output component, the at least one data processor coupled to the at least one user output component; wherein the processing instructions cause the at least one data processor to: in response to data received from the at least one computing device via the wireless communication subsystem, present an indication of the received data at the at least one user output component for communication to the user.

In accordance with an aspect of embodiments described herein, the wearable computing device comprises at least one data storage subsystem secured to the resilient strap within the waterproof storage volume, the at least one data processor coupled to the at least one data storage subsystem. The processing instructions cause the at least one data processor to store at least one of the calculated plurality of swimming metrics in the at least one data storage subsystem.

In accordance with an aspect of embodiments described herein, there is provided a system with a wearable computing device for wearing on a head of a user, the wearable computing device attaching to a resilient strap with a waterproof storage volume, the resilient strap sized to fit around at least a part of a circumference of a human head. At least one sensor is secured to the resilient strap within the waterproof storage volume. At least one data processor secured to the resilient strap within the waterproof storage volume coupled to the at least one user output component, and coupled to at least one non-transitory computer readable medium. The device transmits the sensor data to external devices for further processing and, in some examples, may calculate a plurality of swimming metrics based at least partly on data received from the at least one sensor. The external device may be a cloud processor, computing device, hub 14 and so on. The processing instructions of the wearable computing device cause the at least one data processor to transmit at least one of the calculated plurality of swimming metrics to the at least one computing device via the wireless communication subsystem.

In accordance with an aspect of embodiments described herein, there is provided a method of determining at least one swimming metric in a head-mountable wearable computing device attachable to a resilient strap sized to fit around at least a part of a circumference of a human head. The method may involve the head-mountable wearable computing device receiving data from at least one sensor mounted to the resilient strap, the at least one sensor comprising at least one gyroscope; and the head-mountable wearable computing device calculating a plurality of swimming metrics based at least partly on data received from the at least one sensor.

In accordance with an aspect of embodiments described herein, there is provided a wearable computing device for wearing on a head of a user. The device attaches to a resilient strap and has a waterproof storage volume. The resilient strap sized to fit around at least a part of a circumference of a human head. The waterproof storage volume houses a plurality of sensors and is secured to the resilient strap. The sensors may be an accelerometer, gyroscope, and magnetometer. A wireless communication subsystem is secured to the resilient strap within the waterproof storage volume. The device has a user output component and at least one data processor within the waterproof storage volume coupled to the wireless communication subsystem, coupled to the at least one user output component, and coupled to at least one non-transitory computer readable medium containing processing instructions for execution by the at least one data processor. The data processor may calculate a plurality of swimming metrics based at least partly on data received from the plurality of sensors; transmit at least one of the calculated plurality of swimming metrics to at least one computing device via the wireless communication subsystem; and present an indication of at least one of the calculated plurality of swimming metrics at the at least one user output component for communication to the user.

In accordance with another aspect of embodiments described herein, there is provided a system with a wearable computing device and at least one computing device. The processing instructions of the wearable computing device cause the at least one data processor to transmit at least one of the calculated plurality of swimming metrics to the at least one computing device via the wireless communication subsystem.

In accordance with another aspect of embodiments described herein, there is provided a method of determining at least one swimming metric in a head-mountable wearable computing device comprising a resilient strap sized to fit around at least a part of a circumference of a human head, the method comprising: the head-mountable wearable computing device receiving data from a plurality of sensors mounted to resilient strap. A variety of sensors may be used such as at least one accelerometer, at least one gyroscope, and so on. The head-mountable wearable computing device calculates swimming metrics based at least partly on data received from the plurality of sensors. The head-mountable wearable computing device wirelessly transmitting at least one of the calculated plurality of swimming metrics to at least one computing device. The head-mountable wearable computing device presenting an indication of at least one of the calculated plurality of swimming metrics at least one user output component of the wearable computing device for communication to the user.

In accordance with another aspect of embodiments described herein, there is provided a wearable computing device for wearing on a head of a user, the device comprising: at least one strap connection for connecting to a resilient strap, the resilient strap sized to fit around at least a part of a circumference of a human head; a waterproof storage volume secured to the connector; at least one sensor secured to or within the waterproof storage volume; a power supply within the waterproof storage volume; a wireless transceiver within or secured to the waterproof storage volume for wireless communication with at least one external device; at least one data processor secured within the waterproof storage volume coupled to at least one user output component, and coupled to at least one non-transitory computer readable medium containing processing instructions that when executed by the at least one data processor, cause the at least one data processor to: (i) calculate a plurality of performance metrics based at least partly on the sensor data and transmit at least a portion of the calculated performance metrics to the external device; or (ii) transmit at least a portion of sensor data received from the at least one sensor to the external device configured to calculate the plurality of performance metrics based at least partly on the sensor data.

In some embodiments, the wearable computing device has a wireless communication subsystem within the waterproof storage volume, the at least one data processor coupled to the wireless communication subsystem; wherein the processing instructions cause the at least one data processor to: transmit at least one of the calculated plurality of performance metrics to at least one computing device via the wireless communication subsystem.

In some embodiments, the wearable computing device has at least one user output component, the at least one data processor coupled to the at least one user output component; wherein the processing instructions cause the at least one data processor to: in response to data received from the at least one computing device via the wireless communication subsystem, present an indication of the received data at the at least one user output component for communication to the user.

In some embodiments, the wearable computing device has at least one data storage subsystem within the waterproof storage volume, the at least one data processor coupled to the at least one data storage subsystem; wherein the processing instructions cause the at least one data processor to: store at least one of the calculated plurality of performance metrics in the at least one data storage subsystem.

In some embodiments, the at least one sensor comprises at least one accelerometer or at least one gyroscope.

In some embodiments, the at least one sensor comprises at least one magnetometer.

In some embodiments, the wearable computing device has at least one user output component, the at least one data processor coupled to the at least one user output component; wherein the processing instructions cause the at least one data processor to: present an indication of at least one of the calculated plurality of performance metrics at the at least one user output component for communication to the user.

In some embodiments, the resilient strap comprises first and second strap ends, the waterproof storage volume situated between the first and second strap ends, the wearable computing device comprising: an eye-goggle frame comprising a pair of goggle lens apertures and first and second goggle frame ends, a portion of the eye-goggle frame surrounding each goggle lens aperture retaining a respective goggle lens, each of the first and second strap ends secured to a respective one of the first and second goggle frame ends.

In some embodiments, the waterproof storage volume is situated along the strap opposite the eye-goggle frame.

In some embodiments, the at least one user output component comprises at least one display applied to at least one of the goggle lenses, the at least one display coupled to the at least one data processor, the presenting comprising displaying the indication of the at least one of the calculated plurality of performance metrics on the display.

In some embodiments, the presenting is updated with the indication of the at least one of the calculated plurality of performance metrics in real-time.

In some embodiments, the at least one display is positioned at a periphery of the respective at least one goggle lens.

In some embodiments, the at least one user output component comprises at least one waterproof headphone connected to the strap and coupled to the at least one data processor.

In some embodiments, the waterproof storage volume comprises at least one enclosed interior cavity integrally defined within the strap.

In some embodiments, the wearable computing device has a rigid waterproof enclosure defining a waterproof enclosure interior, the enclosure secured to the strap within the enclosed interior cavity; wherein each of the at least one sensor, the at least one data processor, and the at least one non-transitory computer readable medium are housed within the waterproof enclosure interior.

In some embodiments, the calculated plurality of performance metrics are swimming metrics comprising at least one of stroke count, stroke rate, distance per stroke, swim times and swim splits, stroke type, distance underwater, push-off distance, distance per stroke, stroke rate, cadence, breathing pattern, breaths per length, speed, position, heart rate, horizontal drift, turn time, calories burned, lactic acid, kick rate, GPS tracking, swim time, rest time, workout time, total distance swam, pitch, yaw, roll, linear velocity, stroke profile, and technical velocity.

In some embodiments, the wearable computing device has an heart rate monitor sensor connected to the strap and coupled to the at least one data processor.

In accordance with another aspect of embodiments described herein, there is provided a system comprising: a plurality of wearable computing devices, each for wearing on a head of a user and comprising: at least one strap connection for connecting to a resilient strap, the resilient strap sized to fit around at least a part of a circumference of a human head; a waterproof storage volume secured to the at least one strap connection; at least one sensor secured to or within the waterproof storage volume; and at least one data processor within the waterproof storage volume coupled to at least one user output component, and coupled to at least one non-transitory computer readable medium containing processing instructions executed by the at least one data processor; at least one computing device in wireless communication with one or more of the plurality of wearable computing devices; wherein the processing instructions of each of the wearable computing devices cause the at least one data processor to (i) calculate a plurality of performance metrics based at least partly on the sensor data and transmit at least a portion of the calculated performance metrics to the external device; or (ii) transmit at least a portion of sensor data received from the at least one sensor to the external device configured to calculate the plurality of performance metrics based at least partly on the sensor data.

In some embodiments, the wearable computing device has at least one user output component, the at least one data processor coupled to the at least one user output component; wherein the processing instructions cause the at least one data processor to: in response to data received from the at least one computing device via the wireless communication subsystem, present an indication of the received data at the at least one user output component for communication to the user.

In some embodiments, the at least one computing device associates the transmitted at least one of the calculated plurality of performance metrics with a user profile.

In some embodiments, each wearable computing device is identified by a user identifier and the portion of sensor data or the portion of performance metrics is linked to the user identifier of the respective wearable computing device.

In some embodiments, the wearable computing device has a corresponding computing device of the at least one computing device, wherein the at least one computing device comprises a mobile device with a performance application, wherein the system further comprises at least on at least one computing hub connected to the at least one computing device, the at least one computing device transmitting the portion of sensor data or the portion of performance metrics to the computing hub.

In some embodiments, the system has a cloud data server connected to the at least one computing hub to receive the portion of sensor data or the portion of performance metrics.

In some embodiments, the system has a coach device connected to the at least one computing hub or the mobile device to receive the portion of sensor data or the portion of performance metrics.

In some embodiments, the calculated plurality of performance metrics are swimming metrics comprising at least one of stroke count, stroke rate, distance per stroke, swim times and swim splits, stroke type, distance underwater, push-off distance, distance per stroke, stroke rate, cadence, breathing pattern, breaths per length, speed, position, heart rate, horizontal drift, turn time, calories burned, lactic acid, kick rate, GPS tracking, swim time, rest time, workout time, total distance swam, pitch, yaw, roll, linear velocity, stroke profile, and technical velocity.

In accordance with another aspect of embodiments described herein, there is provided a method of determining at least one performance metric in a head-mountable wearable computing device comprising a resilient strap sized to fit around at least a part of a circumference of a human head, the method comprising: the head-mountable wearable computing device receiving data from at least one sensor detachably mounted to the resilient strap; the head-mountable wearable computing device calculating a plurality of performance metrics based at least partly on data received from the at least one sensor, or transmitting raw data to an external device for calculation of the plurality of performance metrics; and the head-mountable wearable computing device providing feedback based on the calculated performance metrics.

In some embodiments, the performance metrics are swimming metrics, wherein the calculating comprises determining swimming stroke type based at least partly on the data received from the at least one sensor being indicative of movement of a head of a user of the wearable computing device.

In some embodiments, the performance metrics are swimming metrics, wherein the calculating comprises detecting at least one swimming turn movement of a user of the wearable computing device based at least partly on the data received from the at least one sensor being indicative of at least angular velocity and linear acceleration of a head of a user of the wearable computing device to determine performance metrics for the turn movement.

In some embodiments, the performance metrics are swimming metrics, wherein the calculating comprises detecting at least one swimming turn movement of a user of the wearable computing device based at least partly on the data received from the at least one sensor being indicative of a sequence of events comprising a reduction in determined speed to zero velocity and a sensed push-off movement.

In some embodiments, the performance metrics are swimming metrics, wherein the calculating comprises determining swimming velocity based at least partly on the data received from the at least one sensor.

In some embodiments, the head-mountable wearable computing device wirelessly transmitting at least one of the calculated plurality of performance metrics to at least one computing device.

In some embodiments, the head-mountable wearable computing device presenting an indication of at least one of the calculated plurality of performance metrics at least one user output component of the wearable computing device for communication to the user.

In some embodiments, the calculated plurality of performance metrics are swimming metrics comprising at least stroke count, the stroke count calculated based on movement data for motion of the head, the movement data represented as the sensor data.

In some embodiments, the system has the calculated plurality of performance metrics are swimming metrics comprising at least stroke type, the stroke count calculated based on a distance underwater of the wearable computing device and a number of strokes per length, the distance underwater and the number of strokes per length determined from the sensor data.

In some embodiments, the system has the calculated plurality of performance metrics are swimming metrics comprising at least stroke rate, the stroke rate calculated based on movement data for motion of the head, the movement data represented as the sensor data.

In some embodiments, the calculated plurality of performance metrics are swimming metrics comprising at least distance per stroke represented as the sensor data.

In some embodiments, the calculated plurality of performance metrics are swimming metrics comprising at least one of stroke count, stroke rate, distance per stroke, swim times and swim splits, stroke type, distance underwater, push-off distance, distance per stroke, stroke rate, cadence, breathing pattern, breaths per length, speed, position, heart rate, horizontal drift, turn time, calories burned, lactic acid, kick rate, GPS tracking, swim time, rest time, workout time, total distance swam, pitch, yaw, roll, linear velocity, stroke profile, and technical velocity.

In some embodiments, the method involves processing the calculated performance metrics to identify one or more performance efficiencies and generating feedback notification based on the one or more performance efficiencies.

In some embodiments, the presenting is updated in real-time.

In accordance with another aspect of embodiments described herein, there is provided a wearable computing device for wearing on a head of a user, the device comprising: at least one resilient strap comprising a waterproof storage volume, the resilient strap sized to fit around at least a part of a circumference of a human head; at least one sensor secured to the at least one resilient strap and within the waterproof storage volume; a power supply within the waterproof storage volume; a wireless transceiver secured to the at least one resilient strap or within the waterproof storage volume for wireless communication with at least one external device; at least one data processor secured to the at least one resilient strap and within the waterproof storage volume coupled to at least one user output component, and coupled to at least one non-transitory computer readable medium containing processing instructions that when executed by the at least one data processor, cause the at least one data processor to: (i) calculate a plurality of performance metrics based at least partly on the sensor data and transmit at least a portion of the calculated performance metrics to the external device; or (ii) transmit at least a portion of sensor data received from the at least one sensor to the external device configured to calculate the plurality of performance metrics based at least partly on the sensor data.

In some embodiments, the calculated plurality of performance metrics are swimming metrics comprising at least one of stroke count, stroke rate, distance per stroke, swim times and swim splits, stroke type, distance underwater, push-off distance, distance per stroke, stroke rate, cadence, breathing pattern, breaths per length, speed, position, heart rate, horizontal drift, turn time, calories burned, lactic acid, kick rate, GPS tracking, swim time, rest time, workout time, total distance swam, pitch, yaw, roll, linear velocity, stroke profile, and technical velocity.

In some embodiments, the wearable computing device has a wireless communication subsystem within the waterproof storage volume, the at least one data processor coupled to the wireless communication subsystem; wherein the processing instructions cause the at least one data processor to: transmit at least one of the calculated plurality of performance metrics to at least one computing device via the wireless communication subsystem.

In some embodiments, the wearable computing device has at least one user output component, the at least one data processor coupled to the at least one user output component; wherein the processing instructions cause the at least one data processor to: in response to data received from the at least one computing device via the wireless communication subsystem, present an indication of the received data at the at least one user output component for communication to the user.

In some embodiments, the wearable computing device has at least one data storage subsystem within the waterproof storage volume, the at least one data processor coupled to the at least one data storage subsystem; wherein the processing instructions cause the at least one data processor to: store at least one of the calculated plurality of performance metrics in the at least one data storage subsystem.

In some embodiments, the at least one sensor comprises at least one accelerometer or at least one gyroscope.

In some embodiments, the at least one sensor comprises at least one magnetometer.

In some embodiments, the wearable computing device has at least one user output component, the at least one data processor coupled to the at least one user output component; wherein the processing instructions cause the at least one data processor to: present an indication of at least one of the calculated plurality of performance metrics at the at least one user output component for communication to the user.

In some embodiments, the resilient strap comprises first and second strap ends, the waterproof storage volume situated between the first and second strap ends, the wearable computing device comprising: an eye-goggle frame comprising a pair of goggle lens apertures and first and second goggle frame ends, a portion of the eye-goggle frame surrounding each goggle lens aperture retaining a respective goggle lens, each of the first and second strap ends secured to a respective one of the first and second goggle frame ends.

In some embodiments, the waterproof storage volume is situated along the strap opposite the eye-goggle frame.

In some embodiments, the at least one user output component comprises at least one display applied to at least one of the goggle lenses, the at least one display coupled to the at least one data processor, the presenting comprising displaying the indication of the at least one of the calculated plurality of performance metrics on the display.

In some embodiments, the presenting is updated with the indication of the at least one of the calculated plurality of performance metrics in real-time.

In some embodiments, the at least one display is positioned at a periphery of the respective at least one goggle lens.

In some embodiments, the at least one user output component comprises at least one waterproof headphone connected to the strap and coupled to the at least one data processor.

In some embodiments, the waterproof storage volume comprises at least one enclosed interior cavity integrally defined within the strap.

In some embodiments, the wearable computing device has a rigid waterproof enclosure defining a waterproof enclosure interior, the enclosure secured to the strap within the enclosed interior cavity; wherein each of the at least one sensor, the at least one data processor, and the at least one non-transitory computer readable medium are housed within the waterproof enclosure interior.

In some embodiments, the wearable computing device has a heart rate monitor sensor connected to the strap and coupled to the at least one data processor.

In this respect, before explaining at least one embodiment of the invention in detail, it is to be understood that the invention is not limited in its application to the details of construction and to the arrangements of the components set forth in the following description or the examples provided therein, or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

In the drawings, embodiments are illustrated by way of example. It is to be expressly understood that the description and drawings are only for the purpose of illustration and as an aid to understanding, and are not intended as a definition of the limits of the invention.

DETAILED DESCRIPTION

Figure 1:
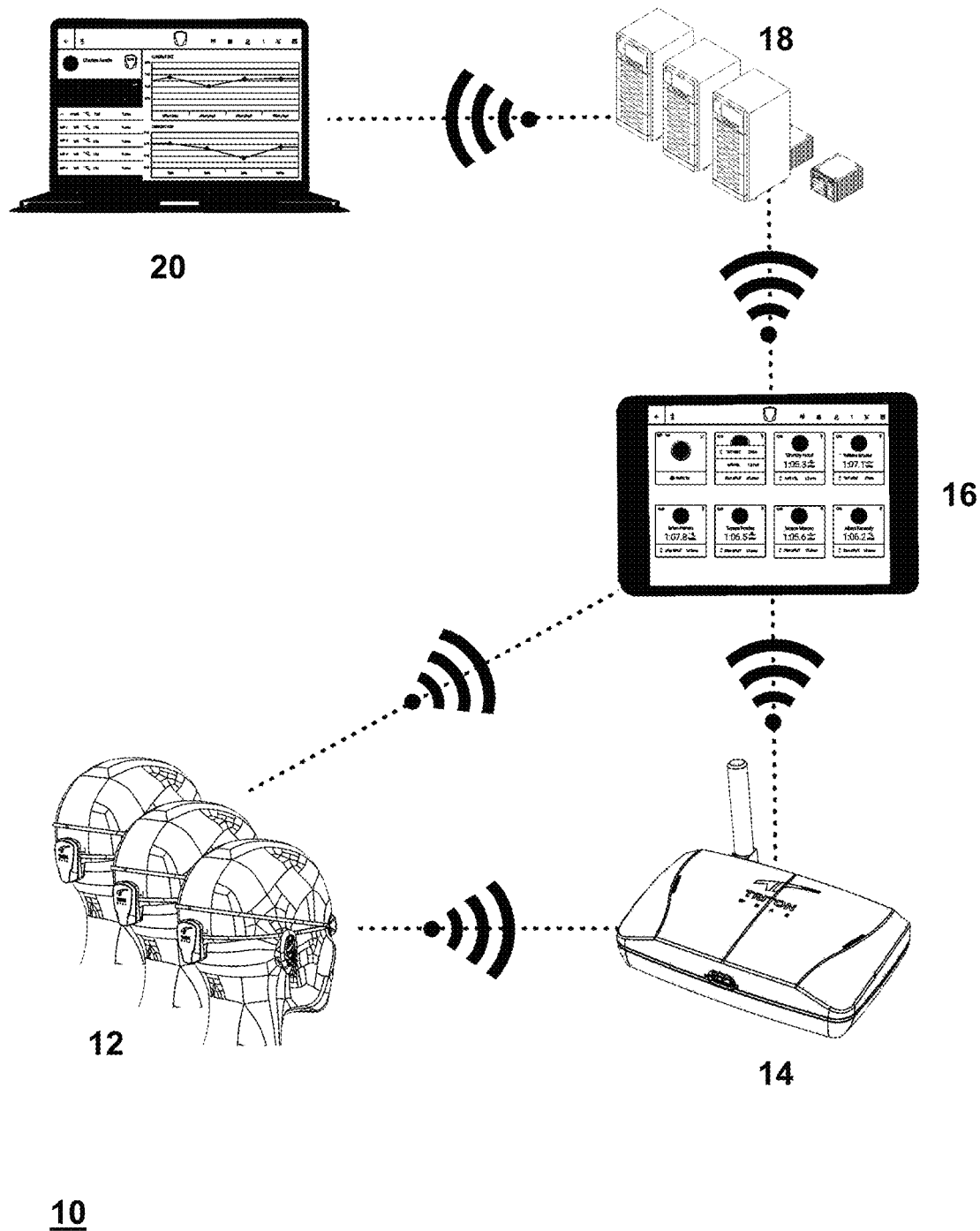
FIG. 1 illustrates a system diagram of the system of an implementation according to some embodiments.

FIG. 1 shows a system 10 of wearable computing devices 12 worn by swimmers as an illustrative example sport. The wearable computing device 12 may also be described herein as a "wearable swimming unit" or "WSU". The present invention may provide for a plurality of wearable swimming units 12 to be used simultaneously and independently, one by each of a plurality of swimmers. Each of the wearable swimming units 12 may communicate data wirelessly with a hub 14 that compiles all of the data from each wearable swimming unit 12 and transmits one signal to a mobile device 16. The data may be generated by one or more sensors included in or in communication with the WSU 12. The data may then be analyzed either by the WSU 12 prior to transmission, or by the hub 14, or by hub 14 one or more other computers, such as computer online servers 18, in communication with the hub 14 or the WSU 12. Where analysis of the data is described herein, it should be understood that in various embodiments of the present invention, the data analysis may be performed by one or more of the WSU 12, hub 14, mobile device 20, and remote computer servers 18, if available.

A wearable computing device 12 is provided that attaches or secures to a resilient strap. The wearable computing device 12 has connectors that enable flexible placement on the resilient strap of goggles in this example. The wearable computing device 12 is detachable from goggles. The wearable computing device 12 may be used with different kinds of goggles. The wearable computing device 12 may attach to a section of the strap in contact with a rear region of the user head for example. There may be other configurations in different embodiments. The wearable computing device 12 has a waterproof storage volume and the resilient strap is sized to fit around at least a part of a circumference of a human head. The device 12 has sensors secured within or to the waterproof storage volume, or otherwise coupled to it. Different example sensors are described (e.g. accelerometer, gyroscope). The sensors may be secured to the resilient strap. The wearable computing device 12 may calculate swimming metrics based at least partly on data received from the at least one sensor. The wearable computing device 12 may include a wireless communication subsystem secured to the resilient strap or the waterproof storage volume and may transmit raw data or calculated swimming metrics to at least one computing device 16, 18 via the wireless communication subsystem. The wearable computing device 12 may include at least one user output component and may present an indication of at least one of the calculated swimming metrics at the at least one user output component for communication to the user. The indication may be audio played in an ear piece connected to the strap, or may be visually displayed on a display in an eye goggle portion of the strap. There may be an audio control secured to the waterproof storage volume. The wearable computing device 12 includes a processor such as a micro-chip to connect components and provide a communication bus. The indication may provide real-time feedback to the user for example.

The system 10 may transform raw sensor data and compute one or more swimming metrics including stroke count, distance per stroke, stroke rate, cadence, breathing count and pattern, splits, heart rate, stroke type, distance swam, time swam, rest time during a workout, horizontal drift, kick rate, distance underwater, turn time, calories burned, lactic acid levels, technical efficiency, stroke profile, linear velocity profile, power cycle, acceleration, speed, position, head position (pitch, yaw, roll), angular velocity, and linear acceleration. The system 10 may be used to (automatically) provide real time feedback of athlete performance to the athlete or the coach during a practice or provide swimming advice or coaching to an individual swimmer using this abundance of data and tracking it over time. The feedback may be audio feedback. The system of the present invention may store all of this data online for tracking a swimmer's performance over time (e.g. throughout the year) by the swimmers and coaches. The system 10 may allow for a coach to analyze data and send notes and information to their athletes based on the tools that may be provided.

The system 10 may also provide a social media aspect where a swimmer can publish or share the swimmer's workout online and on other social media websites. This social media aspect is also used for friends to train together or even compete with each other from around the world or even with strangers in the same pool being able to compete through a unified system. The system 10 may also provide for building workouts as the swimmer swims and allow the swimmer or coach to set goals for a given workout.

The wearable swimming unit 12 may be used in place of a strap on a swimmer's eye goggles. The wearable swimming unit 12 may include one or more sensors and devices, such as an accelerometer, gyroscope, magnetometer, heart-rate monitor, and other sensors. Each WSU 12 may be uniquely associated with a swimmer and may contain a unique identifier ("ID") identifying the swimmer (or other athlete depending on sport) which may be transmitted together with any data from the WSU 12 to a mobile application 16.

System

FIG. 1 shows the WSUs 12, hub 14, and mobile application(s) 16 in wireless communication with one another. Where a single WSU 12 is used, then the WSU 12 may communicate directly with a computing device 16, such as the user's mobile phone, tablet, laptop computer, desktop computer, or other computing device 16. An application, such as a mobile application 16, on the computing device 16 may receive and process data from the WSU 12. Prior to getting into the water to swim, the user may connect the WSU 12 to the computing device. This individual connection may be done via RF and does not require an internet connection as it may pair the devices locally. While the individual swimmer is swimming, the wearable swimming unit may be sending data to the computing device (mobile device). The device does not need to be near the swimmer but if it is water resistant the mobile device could be on the pool deck for the swimmer to keep track of their metrics visually. Once the swimmer has finished their workout, all of the data collected by the wearable unit may be stored in the mobile device 16 until the device is connected to the internet again. Once the device 16 is connected to the internet, the application may automatically upload the data collected from the WSU 12 to a computer server for storage in an online data server 18. This data may then be linked to the swimmer's online profile, at least partly by the computer server 18 associating the received data with the user's unique ID. The swimmer could then access this profile 20 to track their performance over time.

The system flow for multiple WSUs 12 such as in a team environment may be similar as for the individual system flow except for the communication with the mobile device 16 in some example embodiments. As an illustrative example, before practice starts, the coach or group leader may connect a mobile device via Bluetooth to the wireless hub 14. All of the wearable units 12 may then be connected directly to the wireless hub 14 via a local RF connection. This data may be processed on the wireless hub 14 and then sent off to the mobile device 16 through the Bluetooth connection made earlier. The data from all of the WSUs 12 may be viewed live for all swimmers on the mobile application 16. After practice the system works the same as for the individual by uploading all the practice data for each swimmer online automatically which may be linked to each swimmer's respective profile, which may then be viewable to each swimmer and their coach on their online profiles 20.

In an aspect of the embodiments described herein, the wearable computing device 12 secures to a resilient strap and has a waterproof storage volume. The resilient strap may be sized to fit around at least a part of a circumference of a human head. The wearable computing device 12 has a plurality of sensors secured to the resilient strap within the waterproof storage volume. The sensor may be an accelerometer, gyroscope, magnetometer, and so on. A wireless communication subsystem secures to the resilient strap and/or may be within the waterproof storage volume. There may be at least one user output component and at least one data processor (see e.g. FIG. 2) within the waterproof storage volume coupled to the wireless communication subsystem, at least one user output component, and at least one non-transitory computer readable medium containing processing instructions. The processing instructions cause the at least one data processor to pre-process raw sensor data for transmission to mobile device 16 or cloud server 18. The processing instructions may also calculate swimming metrics based at least partly on data received from the sensors. The device 12 may then transmit the calculated swimming metrics to a computing device (with profile 20) via the wireless communication subsystem and present an indication of the calculated plurality of swimming metrics to the at least one user output component for communication to the user.

Some embodiments may include eye-goggle portions, in other embodiments, the wearable computing device 12 may not necessarily include eye-goggles components. In such implementations, the WSU 12 may be a strap worn on the swimmer's head with the sensors and other computing electronics secured in a waterproof storage volume to the strap. In such a case, the user output component may comprise headphones, such as bone conducting headphones, in order to present the swimming metrics or instructions to the user while swimming.

In other embodiments, the resilient strap may include first and second strap ends, the waterproof storage volume situated between the first and second strap ends. In some example embodiments, the wearable computing device 12 attaches to the strap. In other example embodiments, the wearable computing device 12 attaches to an eye-goggle frame with a pair of goggle lens apertures and first and second goggle frame ends. A portion of the eye-goggle frame surrounds each goggle lens aperture retaining a respective goggle lens, each of the first and second strap ends secured to a respective one of the first and second goggle frame ends. The waterproof storage volume may be situated along the strap opposite the eye-goggle frame. The user output component may comprise at least one display (such as a transparent light emitting diode (LED) display) applied to at least one of the goggle lenses. The display may be coupled to the at least one data processor. The indication may be displayed via a HUD (FIG. 16) for example to show a calculated plurality of swimming metrics on the display. Optionally, the presenting may be updated with the indication of the at least one of the calculated plurality of swimming metrics in real-time. Optionally, the at least one display may be positioned at a periphery of the respective at least one goggle lens.

The waterproof storage volume may comprise at least one enclosed interior cavity integrally defined within the strap. The wearable computing device 12 may further include a rigid waterproof enclosure defining a waterproof enclosure interior, the enclosure secured to the strap within the enclosed interior cavity; wherein each of the plurality of sensors, the wireless communication subsystem, the at least one data processor, and the at least one non-transitory computer readable medium are housed within the waterproof enclosure interior.

The wearable computing device 12 may include a heart rate monitor sensor (such as infrared or optical) connected to the strap and coupled to the at least one data processor. The heart rate monitor may be positioned at a respective ear lobe or temple of the user.

The user output component may include at least one waterproof bone-conducting headphone connected to the strap and coupled to the at least one data processor.

The processing instructions may further cause the at least one data processor to: in response to data received from the at least one computing device 16 via the wireless communication subsystem, present an indication of the received data at the at least one user output component for communication to the user. In this way, swimming metrics determined by the wearable computing device 12 may be presented aurally or visually to the user and instructions or other data received from another computing device, such as the hub 14 device, may be presented to the user as well, either simultaneously, or alternately with the other swimming metrics. For example, all audio/video feedback for swimming metrics determined by the wearable computing device 12 may be presented to the user at the wearable computing device 12, without relying on any data or data processing from a separate computing device. However, any data received from a separate computing device 16, 18 by the wearable computing device 12 may also be presented at the wearable computing device 12 as described.

Hardware

The wearable swimming unit (WSU 12) will be fully waterproof in order to protect the electronic components within as well as the athlete. The waterproofing can either be done by: (1) enclosing the electronic components in a rigid enclosure that is then filled with a waterproof chemical compound that allows the electronics to function but protects them from exposure to the environment (i.e. water); or (2) enclosing the electronic components in a rigid enclosure and then over molding the rigid enclosure in a waterproof compound to protect the electronic components from exposure; or (3) enclosing the electronic components in a rigid enclosure and sealing it with a gasket and lid which would be press fit or screw tightened in order to create a water proof seal. It should be understood that any of these or other options may be employed. In particular, in embodiments where the rigid enclosure is provided protection for the components housed within may be increased over embodiments where no rigid enclosure is provided.

A non-exhaustive list of the electronic components (including sensors) which may be provided in the WSU 12 includes: a 6-axis Inertial Measurement Unit (3-Axis Digital Accelerometer, and a 3-Axis Digital Gyroscope) or a 9-axis Inertial Measurement Unit (3-Axis Digital Accelerometer, a 3-Axis Digital Gyroscope, and a 3-Axis Digital Magnetometer); a Microcontroller (e.g. Cortex-M4F microcontroller such as the STM32F429 from ST); off-microcontroller storage to store metrics and media (e.g. NOR/NAND SPI Flash); a wireless module to transmit calculated metrics to the hub, and new settings from the hub 14 to the WSU 12 (e.g. 868/915 Mhz radio); a real-time clock to ensure synchronized timing of metrics and events; a Lithium Ion Polymer Battery with a Battery Charging circuit; a USB interface to communicate with the device for firmware updates, and to provide power for charging; a PCB. This is an illustrative example embodiment.

Figure 2:
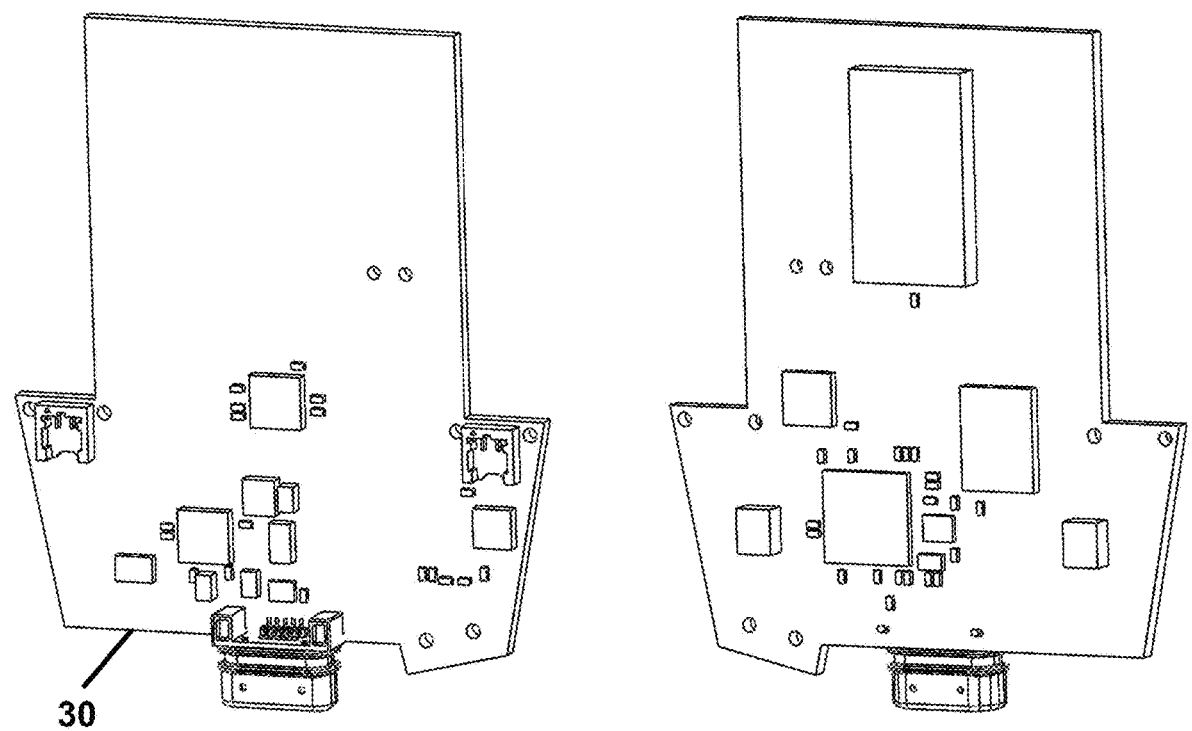
FIG. 2 illustrates a processor implementation according to some embodiments.

The waterproof unit may contain sensors such as the gyroscope and accelerometer and a magnetometer, for examples. The data from these sensors may be processed via a micro-controller on the circuit board (FIG. 2). There may also be additional off-microcontroller memory within this unit used for storing media, user configuration information, and long term metric storage. The WSU 12 may include a wireless communication module for communicating either with the hub 14 or a mobile device 16 directly. This wireless module may communicate via WiFi, Bluetooth or another custom protocol to allow multiple units to be wirelessly connected to one another or to one or more hub(s) 14 and mobile device(s) 16. The WSU 12 may also include at least one battery to power the components and a charging circuit to allow the unit to be charged. These components are shown in the embodiment shown in FIG. 2 which shows an example circuit board image layout. Note that the exact size and number of components may be varied and are shown for illustrative purposes. For example, each of the sensors and electrical components provided in the WSU 12 may be connected to and located on a single PCB.

The WSU 12 may be used independently of any other computing device, to log any determined swimming metrics for real-time or later access at the WSU 12.

There may be additional hardware components such as for example:
Multiple accelerometers, gyroscopes, magnetometers to allow for advanced noise reduction techniques;
An infrared to optical heart rate monitor to provide further metrics surrounding the athlete's performance;
Feedback mechanism(s) to provide feedback to the athlete through audio (through an audio module and bone conduction headphones) or haptic feedback (through a vibration motor);
GPS and 3G/GSM to collect and transmit data in outdoor environments where greater distances are covered by the athlete and greater transmission range is required to transmit the metrics back to the coach;

A barometric sensor or digital compass to account for error (e.g. drift) from the inertial measurement units over time; and Other sensors required to determine any other performance metrics or biometrics.

RF Protocol

The WSU 12 may communicate directly with a mobile device 16 (in the event of a single WSU 12—mobile device configuration), or through a hub 14 (in the event of a multi WSU 12—mobile device configuration).

During direct communication with a mobile device 16, a high level RF communication protocol may be used (e.g. Bluetooth). The benefit of using a high level protocol such as Bluetooth is that most mobile devices 16 already enable the protocol for communication, and minimal configuration may be required on the mobile device side to communicate with the WSU 12.

However, in a multi WSU 12—mobile device configuration, high level protocols such as Bluetooth may be cumbersome to work with due to the overhead required on both sides to navigate the layers in the protocol stack. In such events a simpler streamlined protocol may be used in order to reduce latency and allow for increased bandwidth on the network. As an illustrative example, a connection using the RF protocol may be used in a multi-WSU 12 to mobile configuration.

Example requirements for designing the RF protocol may be as follows:

Little overhead—keep the protocol as simple as possible;

RF needs to be non-blocking—Signal processing events and metric calculation cannot be blocked by RF overhead;

Metric transmission needs to be guaranteed—the WSU 12 cannot skip a metric transmission and needs to ensure that the metric was received by the hub; and The order the metrics are presented to the user are important—metrics need to be presented to the user synchronously (i.e. a latter generated metric cannot be presented prior to an earlier generated one).

The RF technique may include software acknowledgement (ACK). The microcontroller on the transmitter (the WSU 12 or the hub 14) sends a transmission request to the transmission module with a data payload. The module sends the request and gets back to work detecting events and metric calculation (in the case of the WSU 12) or goes to sleep (in the case of the hub). If an ACK hasn't been received, the transmitter retries the transmission event with the same payload. During this process, if additional metrics have been calculated, they are added to a queue on the transmitter. Once an ACK has been received the transmission of the next metric is attempted.

This means of communication is used for almost all the RF transmission use cases, including sending new metrics to the hub 14, syncing to the hub 14 when a WSU 12 comes online, and sending new configuration data to a WSU 12. There are also additional events when a Hub 14 wants to communicate non-critical data to the WSU 12 s (e.g. send swimmer specific setup parameters to a given WSU 12). In this case, the RF protocol uses a pseudo-UDP protocol with no ACK. Use case for this protocol include heartbeat pings on the network, and non-critical configuration data.

Hub

Figure 3:
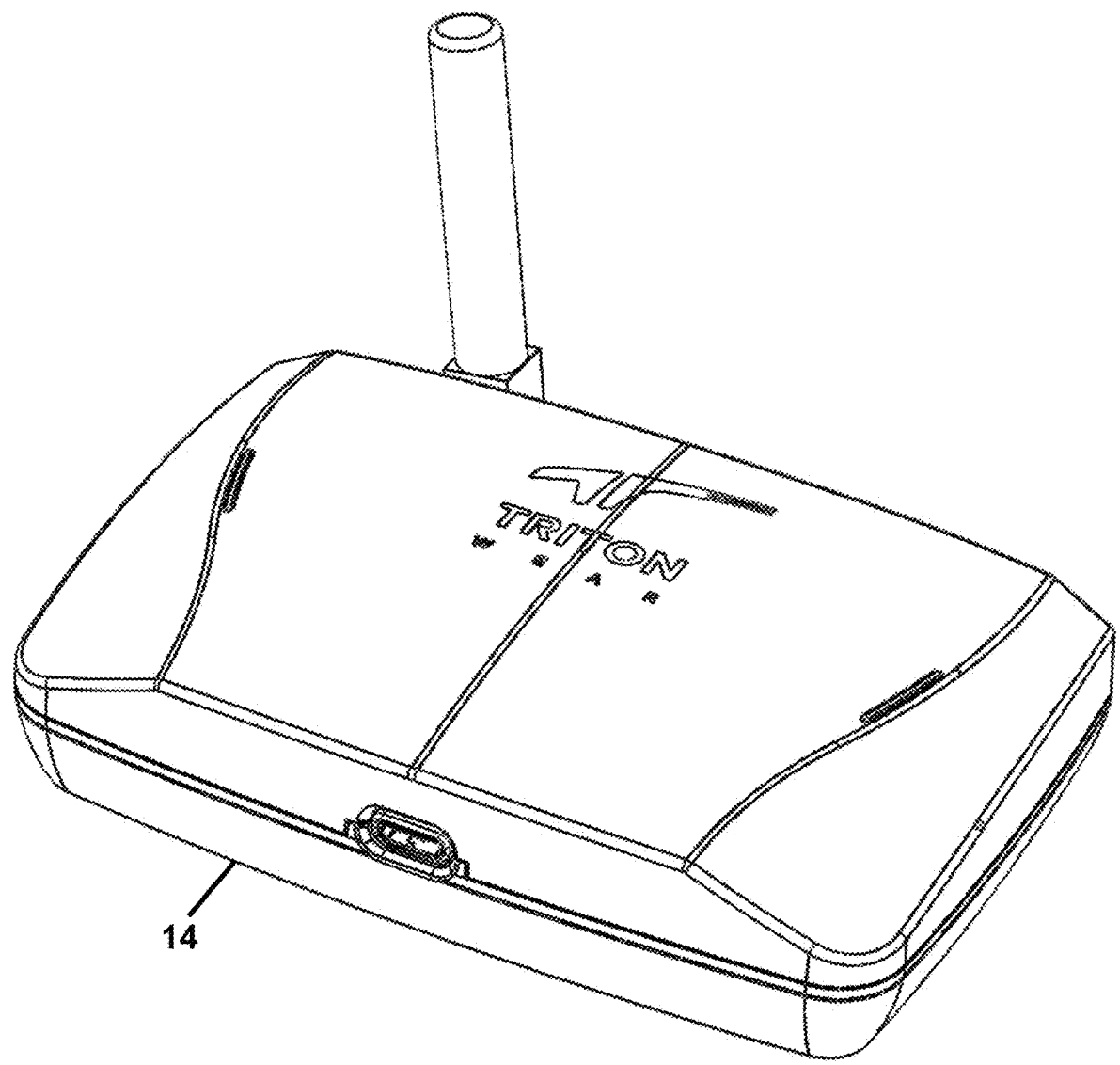
FIG. 3 illustrates a perspective view of a wireless hub device according to some embodiments.
Figure 4:
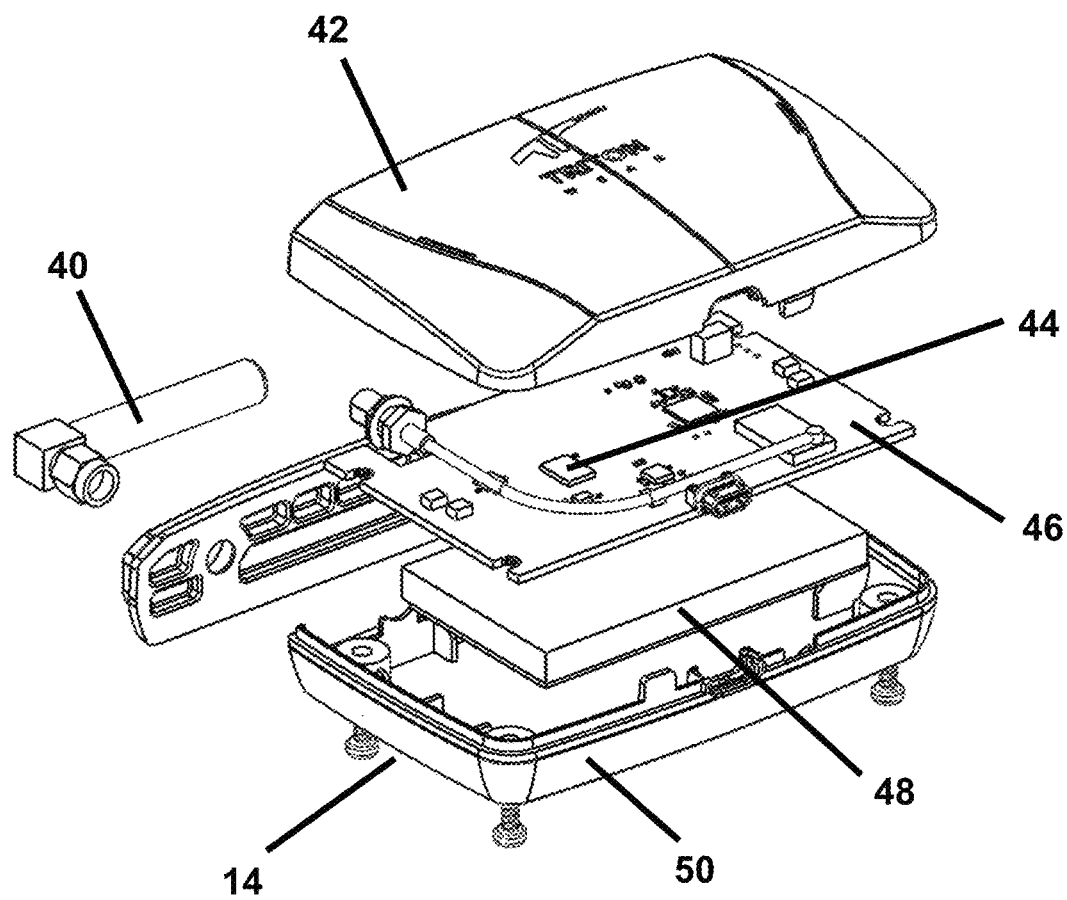
FIG. 4 illustrates an exploded view of a wireless hub device of FIG. 3.

The system 10 may comprise a wireless hub 14, shown in FIGS. 3 and 4, which may be used when multiple WSU 12 s are being used simultaneously on different swimmers and data from multiple WSUs 12 is desired. The hub 14 may be used by teams and coaches but also any other group of swimmers. The hub 14 may connect to multiple WSUs 12, receiving data from each WSU 12 wirelessly via the respective wireless communication modules of each WSU 12, and sending that received data to a device, such as a mobile device used by a swim coach, to display or analyze different swim metrics calculated for each swimmer based on the received data. The wireless hub 14 may also be used as a charging dock for multiple units either with multiple plug-in ports or through wireless charging. Each wireless swimming unit may connect to the wireless hub 14 through a RF connection. The data from all of the units connected to the wireless hub 14 may then be processed and combined on board and then sent to a mobile device 16 via a connection, such as a single Bluetooth connection. The data for every unit and in turn every swimmer may then be displayed on a mobile application 16 which will be explained in further herein. Each unit 12 may be assigned a unique ID linked to the swimmer that wears it so each unit's data may be linked to that unique ID when transferred to the mobile application 16 and may then display that data beside the respective swimmer's name. The hub 14 may include a screen to show the user exactly how many and whose units 12 are connected and possibly other information such as battery levels on each unit. The electronics hardware used in the hub 14 mimic that used in the WSU 12—with the IMU section unpopulated, and the addition of a Bluetooth module for communication with the mobile device.

FIG. 4 shows an exploded view of an example hub 14 with an enclosure lid 50 and an enclosure base 42 providing a waterproof enclosure for PCB 46, battery 48 and Bluetooth 44 RF connection. The hub 14 has an antenna 40 for wireless communication.

Example Design

Figure 5:
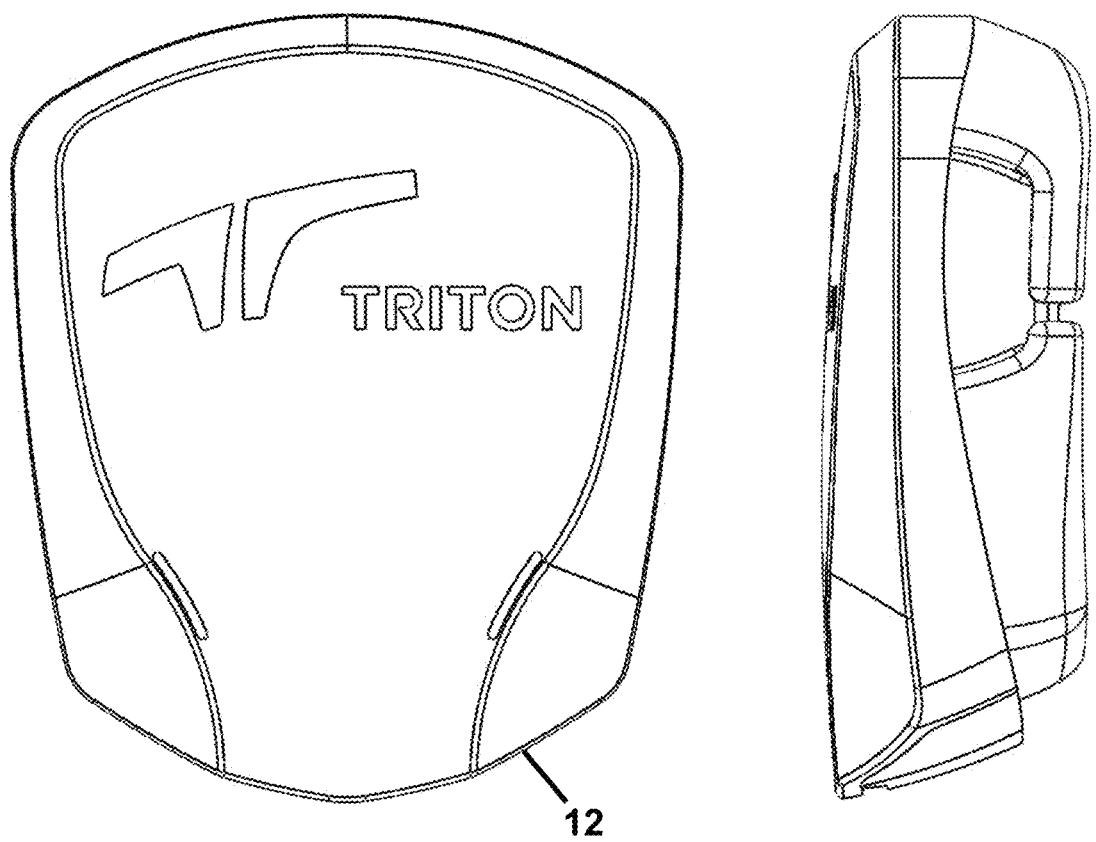
FIG. 5 illustrates a perspective view of a waterproof unit of the wearable swimming unit device according to some embodiments.
Figure 6:
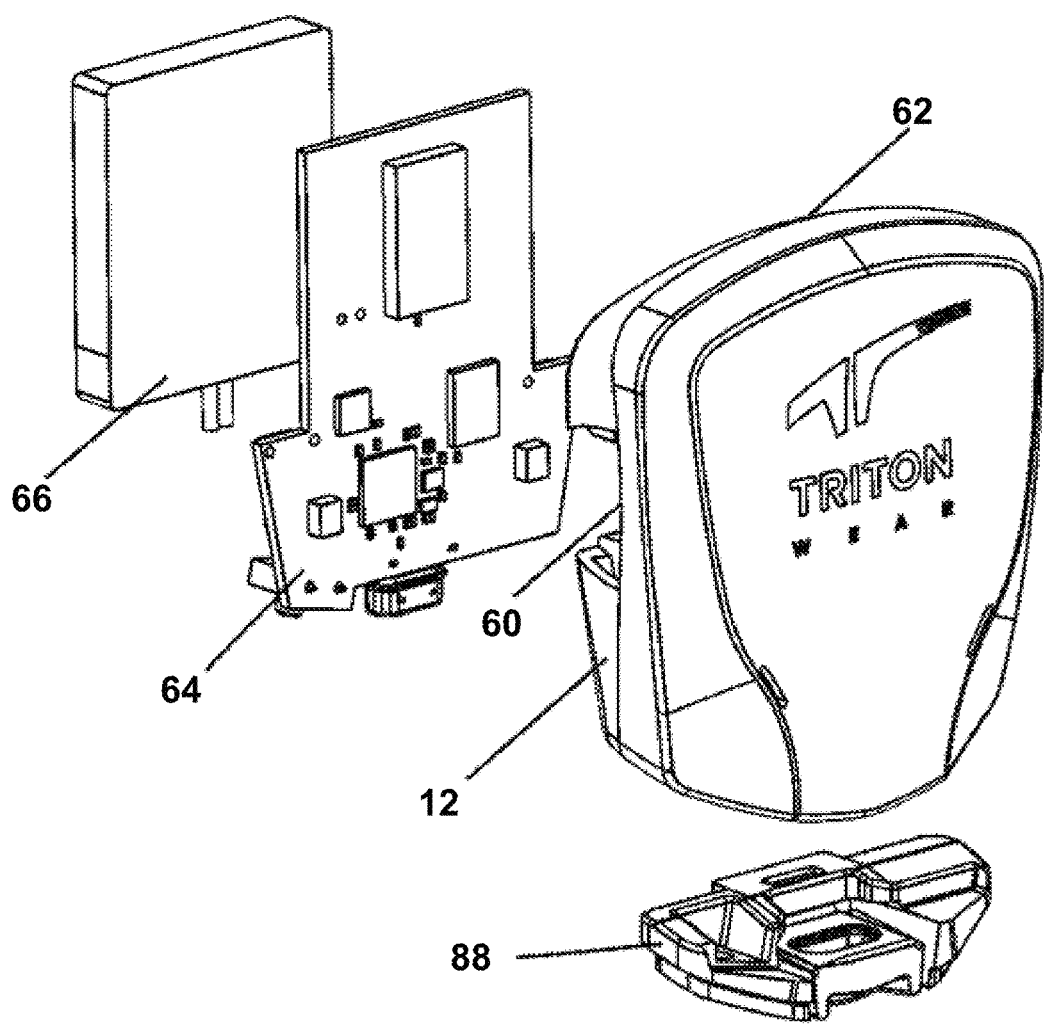
FIG. 6 illustrates an exploded view of the waterproof unit shown in FIG. 5.

Accordingly, as shown in FIG. 5 the WSU 12 may comprise a rigid waterproof enclosure, which may be made of one or more hard plastic structural elements, secured together by screws, bolts, adhesive, sealant, or any other type of securing means resulting in a waterproof seal. Primary electrical components and sensors may be housed within the enclosure as shown in exploded view of FIG. 6. The WSU 12 has an enclosure with an enclosure lid 68 and enclosure base 62. The WSU 12 enclosure houses a battery 66 and PCB 64. The WSU 12 has a connection 60 to secure or attach to a strap, for example. The connection may connect to different sporting equipment for other example applications.

This plastic enclosure may be fully waterproof. Waterproofing of the enclosure may be completed using a method called potting, where a liquid compound is poured over the circuit and battery which solidifies and protects the components from water. Waterproofing may be completed with the use of a gasket and a lid which tightens the gasket against the base of the enclosure to create a waterproof seal. Waterproofing may also be completed using injection molding techniques such as over-molding which creates a mold directly over the board and battery (or over a pod containing to board and batter to provide protection from the heat and pressure of the over-molding process) which then creates a solid assembly which is completely waterproof.

Figure 7:
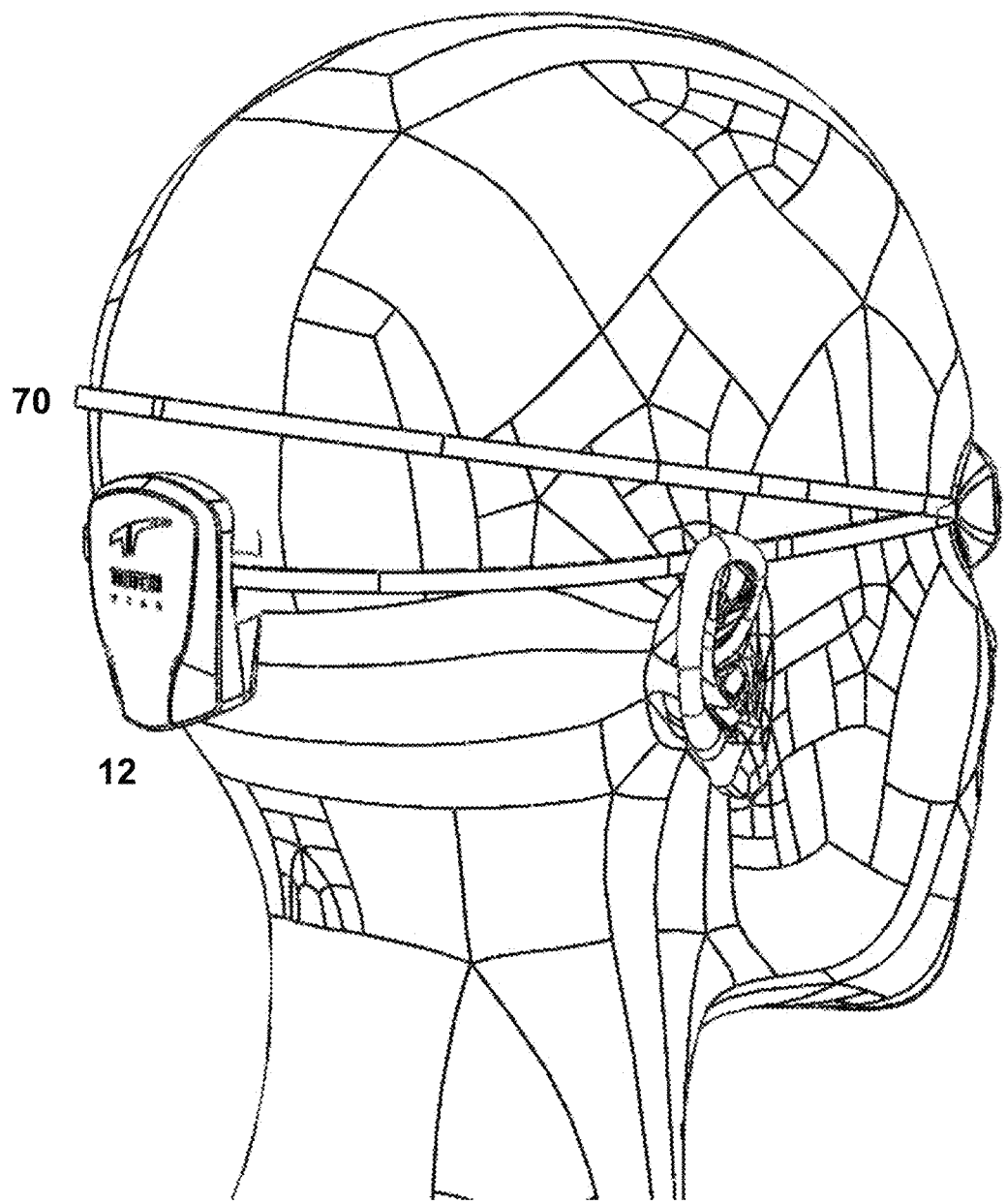
FIG. 7 illustrates a perspective view of an implementation of the wearable swimming unit device as worn by a person.

A diagram of an exemplary embodiment of an assembled WSU 12 of an example embodiment is shown in FIG. 7. The enclosed portion of the WSU 12 may secured to a strap 70 as a standalone unit as shown in FIG. 7, or may form part of the strap 70.

Figure 8:
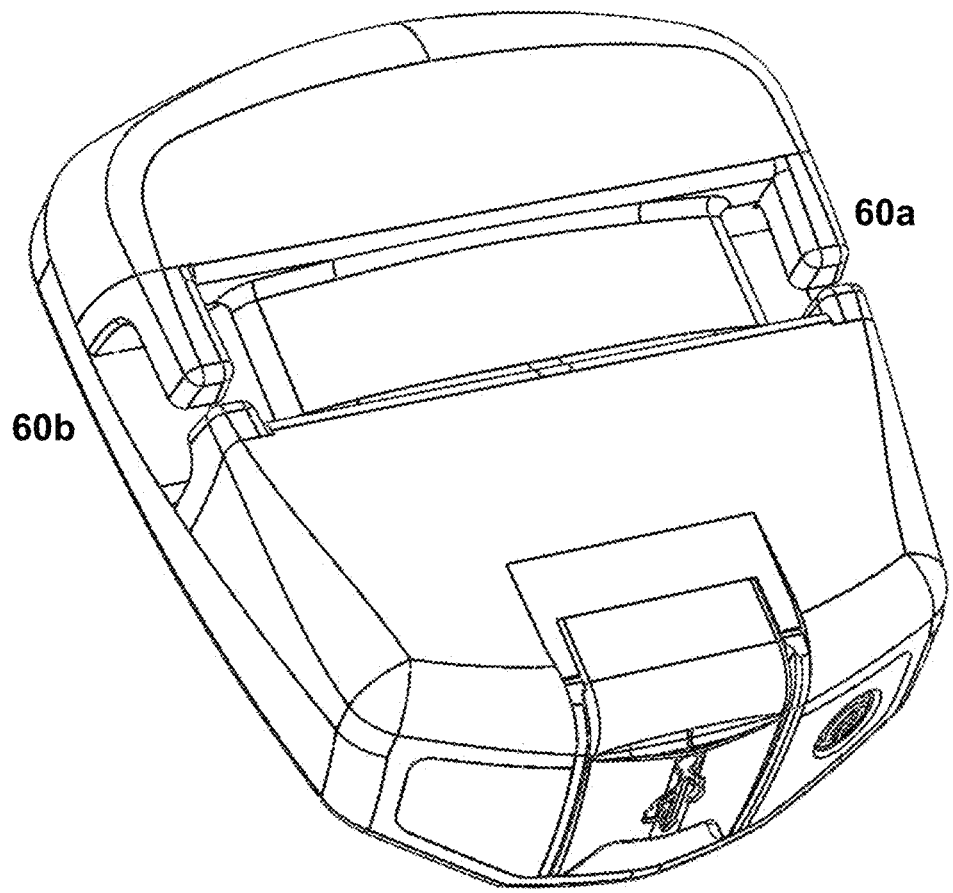
FIG. 8 illustrates a connection implementation according to some embodiments.

The enclosure may be built in a way that is comfortable and not noticeable to the swimmer. The enclosure may also be designed to easily connect to a swimmers goggle strap. One version of the device may include a mechanical connection 60a, 60b with a break in it to allow for a goggle strap to slide through the break and rest in an open volume as shown in FIG. 8.

Figure 9:
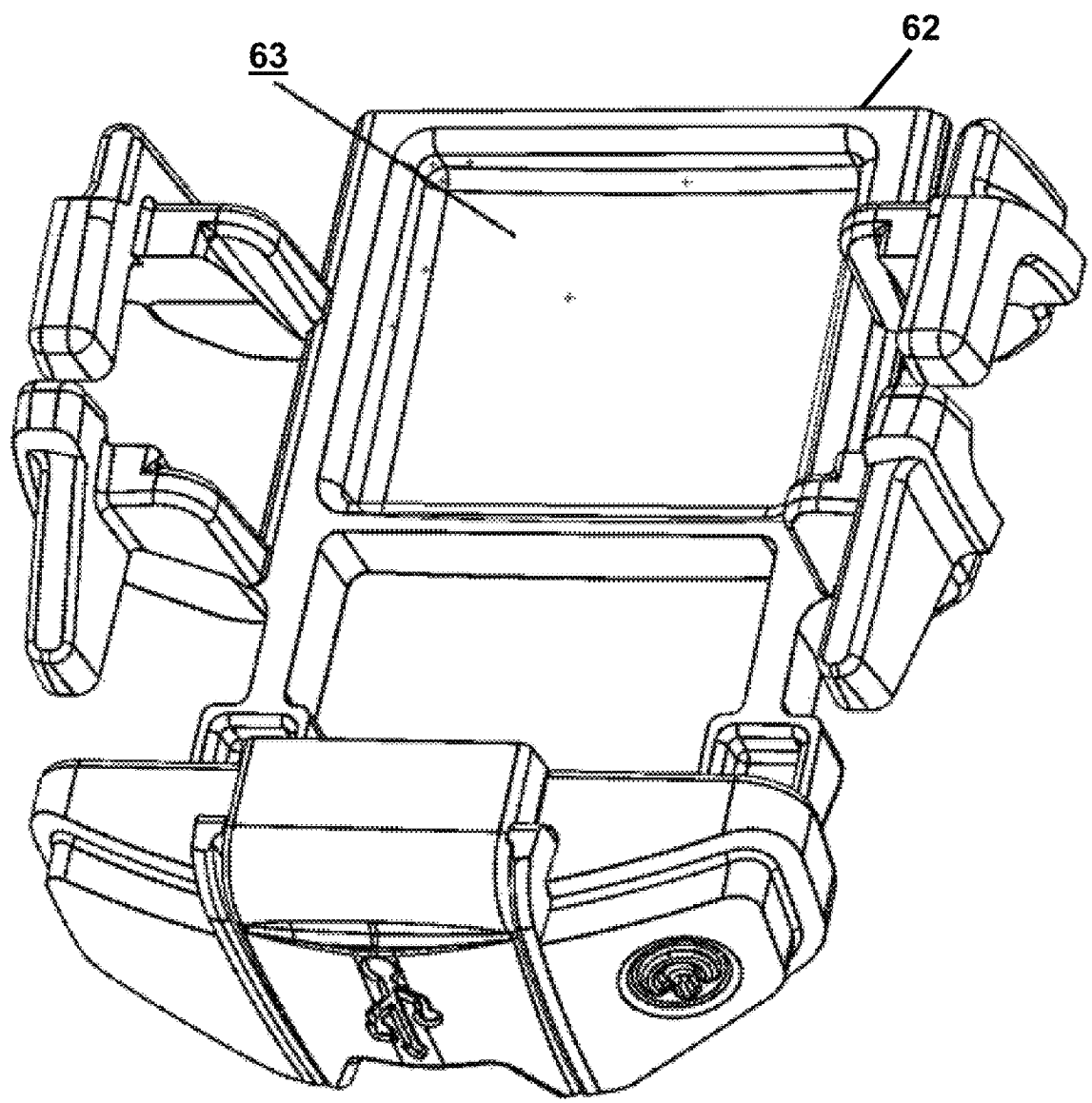
FIG. 9 illustrates an enclosure implementation according to some embodiments.

The RF signal strength may be increased with an appropriate air gap between the RF module and the enclosure. For the gasket and over-mold methods of waterproofing this simply requires the enclosure to be designed to allow a certain air gap to ensure a minimal drop in signal strength. For the potting technique, an air pocket may need to be designed into the enclosure which the board would be sealed against to ensure no potting compound leaked into the pocket. This would allow for the required air gap even with a liquid potting compound being poured over the entire board and battery while still providing the required waterproofing. This air pocket concept can be seen as the region 63 within the enclosure shown in FIG. 9.

Figure 10:
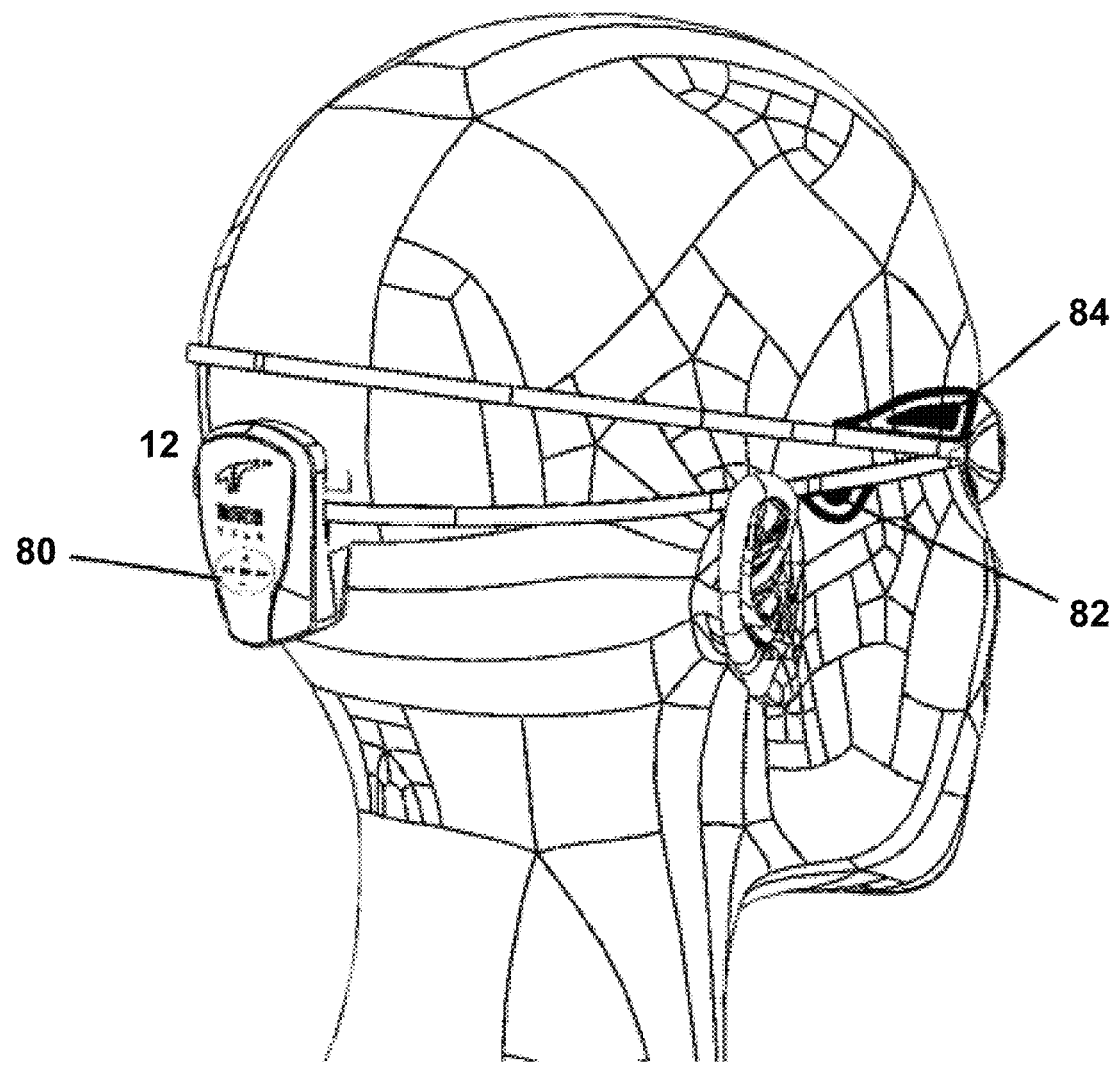
FIGS. 10 and 11 illustrate wearable swimming unit devices according to some embodiments.
Figure 11:
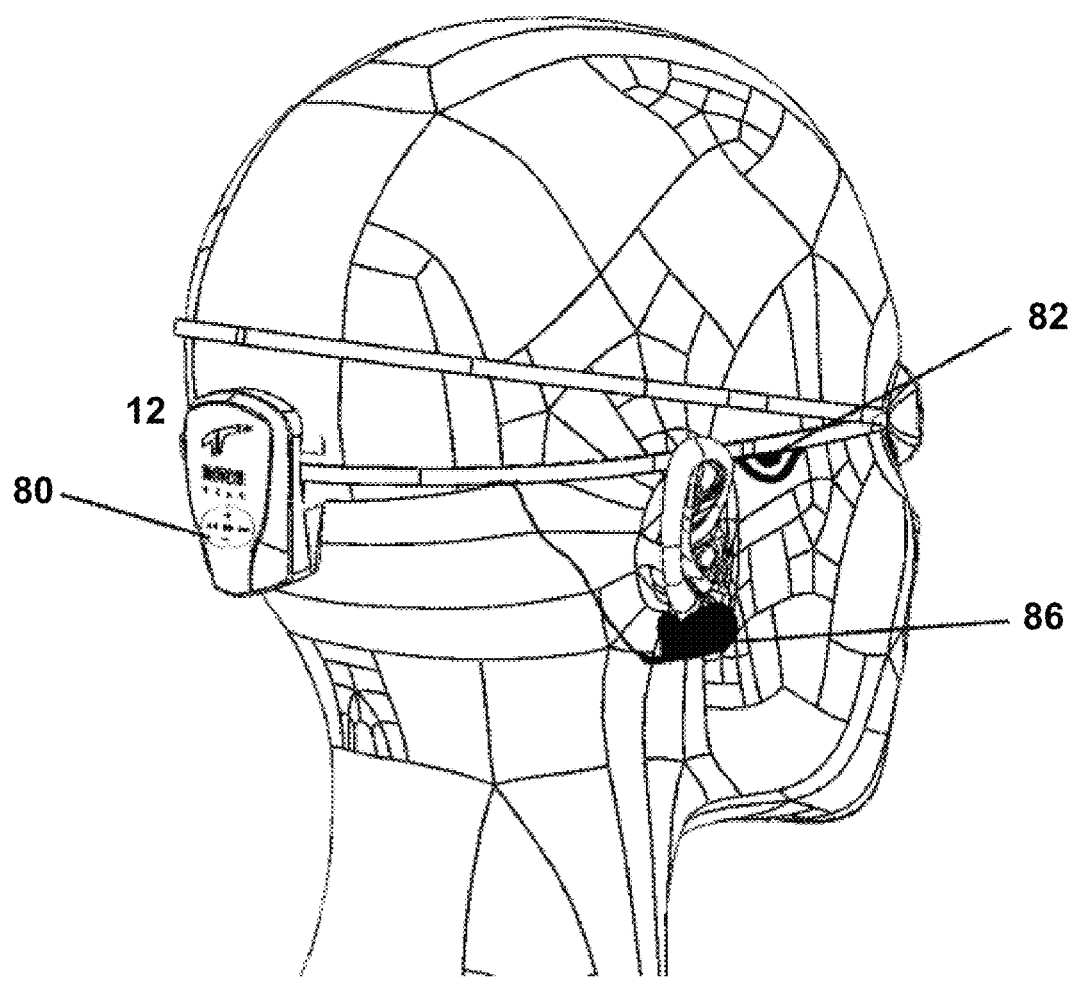

The enclosure may also house or provide a mounting surface for other sensors and devices of the system 10. Optionally, the WSU 12 may be housed inside the strap on the back of the strap when worn on a user's head. There may be an audio control 80 secured to the WSU 12. The enclosure or strap may include one or more buttons on it for controlling various functions such as optional media player functionality of the WSU 12 such as play/pause, volume, and skipping songs. The audio functionality of the unit may be heard through either in-ear headphones or through bone conduction headphones 82, as shown in FIG. 10. A heart rate monitor sensor 84 may also be located within the strap itself, or otherwise attached thereto, separate from the enclosed portion of the WSU 12. The swimmer's heart rate can be taken from two different locations on the swimmer's head: (1) the swimmer's temple, or (2) the swimmer's ear lobe with the use of an infrared (IR) or optical transmitter and receiver. The IR sensor, if employed, may emit light into the skin and then some of that light may be reflected back to a receiver. When blood pulses, the receiver reads a lower light level which then creates a signal with peaks or pulses which is used to calculate beats per minute (BPM). Two different layouts are shown in the figures: FIG. 10 shows the wearable swimming unit using the temple heart rate sensor 84, and FIG. 11 shows the ear lobe heart rate sensor 86. The strap may provide several adjustment points so that the swimmer can locate the heart rate sensor, waterproof unit, and bone conduction headphones in respective locations suitable for the head anatomy (e.g. head size and head shape) of the particular swimmer. The strap may be designed to interface with any goggle as there are many styles of goggles that swimmers prefer. The waterproof unit component of the WSU 12 may be smaller than the unit shown in the figures. The respective sensors may be placed approximately as shown in FIGS. 10 and 11.

Swim Metrics

The wearable swimming unit contains sensors such as accelerometers, gyroscopes, magnetometers and GPS units. The system employs operations to determine key performance metrics based on the movement of the swimmers head. The data from these operations may be combined into further operations to determine swimming metrics with the exception of the swimmer's heart rate. The swimmer's live heart rate may be determined through a sensor on the strap which may either clip onto the swimmer's ear or may be sensed directly from the swimmer's temple. The live swim metrics which may be calculated by the system of the present invention include: stroke count, distance per stroke, stroke rate, cadence, breathing count and pattern, splits, heart rate, stroke type, distance swam, time swam, rest time during a workout, horizontal drift, kick rate, distance underwater, turn time, calories burned, lactic acid levels, technical efficiency, stroke profile, linear velocity profile, power cycle, acceleration, speed, position, head position (pitch, yaw, roll), angular velocity, and linear acceleration. Optionally, a plurality of accelerometers may be provided in the WSU 12. Optionally, a plurality of gyroscopes may be provided in the WSU 12. Optionally, a plurality of magnetometers may be provided in the WSU 12. Optionally, a plurality of GPS units may be provided in the WSU 12.

Various operations may be employed by the system of the present invention to analyze swim metrics.

Swim Metrics: Example Methodology

Similar methods may be used to determine all swim metrics from the raw sensor data. These techniques include filtering techniques, sensor fusion techniques, digital signal processing (DSP) techniques as well as machine learning techniques.

Sensor fusion techniques combine sensory data of different sensors to increase the certainty of the data compared to that of the sensors individually. Sensor fusion techniques that may be used include any or all of central limit theorem, Kalman filters, Bayesian networks, and Dempster-Shafer theory.

DSP techniques may involve the manipulation of data both in the time domain and the frequency domain. These techniques may include any or all of a Bilinear transform, Discrete Fourier transform, Discrete-time Fourier transform, Filter design, Linear time-invariant (LTI) system theory, Minimum phase, Transfer function, Z-transform, Goertzel algorithm, and s-plane analysis.

Machine learning techniques may be used to create processes that can learn from data. For example, a large enough database of swimming raw data combined with known real values may allow for specific metrics like stroke types, stroke events, timing events (starts, turns, stops) to be categorized based on certain confidence levels from the known database. There are many machine learning techniques which may be applied including any or all of decision tree learning, association rule learning, artificial neural networks, inductive logic programming, support vector machines, clustering, Bayesian networks, reinforcement learning, similarity and metric learning, sparse dictionary learning, a hidden Markov model, and genetic algorithms.

These theorems and methodologies provide a non-exhaustive list of techniques that may be used to calculate swim metrics from sensor data in the WSU 12.

Swim Metrics: Swim Times/Splits

The swim times and splits may be broken down into three conditions: a start condition, a turn condition, and a stop condition. Each condition may be determined from multiple characteristics seen from the signals produced by the sensors. These characteristics may differ depending on the stroke type being swam. For the start condition, some of these characteristics may include the swimmers motion as they rotate from being vertical to being horizontal as they push off the wall, which may be followed by a sudden increase in acceleration as the swimmer pushes off the wall and continues at some velocity which may begin a timer. Many error correction techniques may be implemented to minimize or eliminate the occurrence of false positives or false negatives for each of these conditions. One method of error correction for the start condition may be to confirm the swimmer is in fact swimming once a certain number of strokes are detected after the push off event and before a time out timer ends to ensure it was not a false start. The turn condition is when a swimmer turns at the wall and can be broken down into two turn types: freestyle/backstroke turns and butterfly/breaststroke turns. The turn condition may be sensed in the signal produced by the sensors which has a very unique appearance compared to normal swimming. The turn condition also occurs in the middle of two swimming lengths which may show a distinct disturbance in the oscillatory signal where the turn occurs. The turn may further be broken down to a start of turn and an end of turn condition in order to help minimize false positives in turn recognition. The start of turn and end of turn require two sets of characteristics to confirm a turn event which may make it more accurate and/or consistent.

Once this operation determines the turn event, it records the specific time of the event, which subtracted from the previous event (either start or turn condition) is equal to the split time for the length, that split is recorded, but the total swim time timer continues as the swim is likely not over (unless they "finish to their feet" in which case the unit recognizes that they are no longer swimming based on the following end condition methodology). The end condition (when a swimmer stops swimming) is determined based on multiple characteristics in the signal from the sensors. These characteristics may include a spike in acceleration when the swimmer hits the wall, the motion of the swimmers head moving from horizontal to vertical as they finish, as well as the variance and standard deviation of the signal decreasing since the swimmer is no longer oscillating while swimming. Characteristics such as variance and standard deviation may also be used as an error correction method to confirm that the swimmer has in fact stopped and then the signal can be further analyzed to determine the exact time of that end condition based on the other characteristics in the signal such as the deceleration as they hit the wall. Once the end condition time is determined it can be subtracted from the previous condition (either start or turn) in order to determine the split time for that length. The entire repetition time can then be determined by summing all of the split times calculated from the start event to the stop event or by subtracting the time stamp on the end condition from the time stamp on the start condition.

Swim Metrics: Stroke Type

Stroke type may be determined based on the motion of the swimmers head. Each stroke (butterfly, backstroke, breaststroke, and freestyle) has their own unique signal profile which allows them to be sensed consistently for all swimmers. Many methods may be used from threshold characteristics of the signal to machine learning techniques that categorize a signal with a certain level of confidence compared to a large database of known stroke types. Freestyle stroke may be determined based on the rolling motion of the swimmer's head as they stroke and based on their breathing to the left and right of their bodies. Backstroke may be determined in the same way as freestyle based on the rolling motion of the swimmer's head, but the values may be inverted as the swimmer's face may be up out of the pool and there may be no breathing pattern as the swimmer can continuously breathe in backstroke. Breaststroke may be determined based on the unique pull up out of the water and dive back down motion of the stroke combined with the measuring of a power pull-out each length. The butterfly swimming stroke may be determined by the wave-like motion of the stroke and the lack of a power pull-out compared to breaststroke. Butterfly may also have a unique breathing pattern where the swimmer's head may be raised and rotated up out of the water when they breathe compared to having their head down when simply stroking.

An average style for each stroke may be known based on an average pattern, and the unit may learn its individual swimmer's style and technique as they use it. As the unit is used more, it may constantly update key parameters based on the swimmer's technique by using methodologies such as a running average. These parameters may be found by detecting key characteristics in the pattern of either the raw data from the sensors or the pitch, yaw, and roll calculated as each stroke is swam. Each stroke creates an oscillatory pattern about an axis as the swimmer swims through the water. Each stroke has a unique pattern and each swimmer may have a unique pattern for each stroke and the use of parameters calculated for each specific swimmer may increase the accuracy of the operations. There may also be an initial calibration of the unit when it is first purchased where it may have the athlete swim a certain distance of each stroke which may calibrate the system to their specific technique. The parameters that may be used for calibration as well as the parameters used to learn as a swimmer uses the device may include stroke characteristics such as peaks, frequency domain characteristics, and zero crossing locations of their stroke signals. The parameters may also include historical metrics of a given swimmer which may help to provide boundaries or expected values for each metric at different speeds for each stroke for each swimmer.

Swim Metrics: Stroke Count

Stroke Count: The swimmer's stroke count is determined based off the motion of the swimmers head as they stroke through the water. Each stroke type creates a unique oscillatory signal profile (as mentioned in the stroke type section) in the motion sensor data which may be used to determine the occurrence of stroke events. As the swimmer strokes through the water, they create an oscillation in the signal. This consistent oscillation makes it possible to detect the exact time of each stroke event which can then be used to count the number of strokes taken in length. This oscillation in the sensor data may be seen in both the accelerometer and gyroscope signal for all three axes. This may provide 6 separate raw data signals which may be used or manipulated in a variety of ways in order to accurately determine stroke events. These manipulations may be done using any or all DSP and machine learning techniques mentioned earlier in this section.

These oscillatory motions can also be seen through the Euler Angles (pitch, yaw, and roll) which are different for each stroke type. For freestyle, the swimmer rolls their head slightly with each stroke which may be sensed in the roll readings. With backstroke there is a similar roll, but it is less significant than freestyle. Both butterfly and breaststroke have a wave like motion which is read in the pitch measurements. Each time the unit's pitch reading passes a certain limit, a stroke count may be added. The specific limits, or peaks, may be modified automatically as each unit learns the specific technique of the swimmer that owns it.

The system 10 may be able to determine stroke count using acceleration as opposed to angle which allows the unit to be mounted on the head of the swimmer. The present invention may determine more than just stroke count. Optionally, other methods of determining stroke count may also be used.

Swim Metrics: Distance Underwater/Push-Off Distance

Distance underwater is the distance a swimmer travels after pushing off the wall until they break out of the water. This may be measured using the swimmers average velocity over the length (pool length divided by the time taken to swim the length) and the time at which the swimmer breaks out of the water. The breakout may be seen in the various signals and occurs just before the first stroke is taken which may be seen when calculating the strokes taken per lap. Distance underwater would then be calculated by multiplying the time of the breakout event by the average velocity. A more accurate distance underwater may be determined using a live velocity profile over the course of a length multiplied by the break out time. This velocity profile may show a more accurate speed profile while the swimmer is underwater and may result in a higher accuracy distance underwater.

Swim Metrics: Distance Per Stroke

Distance per Stroke: Distance per stroke (DPS) is the distance a swimmer travels through the water with each stroke and is derived from other metrics including stroke count and distance underwater. The average distance per stroke over a length is measured simply by finding the total swimming distance of a length (the pool length minus the distance underwater) and dividing it by the total number of strokes over that length. The length of the pool may be a known variable of the specific pool in use; either short course yards (SCY-25 yards), short course meters (SCM-25 meters), or long course (LC-50 meters). A higher resolution or real time (non-average) DPS may also be found using only the stroke count with the associated time stamps per stroke event combined with the swimmers live/real time velocity which may allow for a profile of DPS to be displayed across a length in case a swimmer changes speed within a given length.

Swim Metrics: Stroke Rate

Stroke rate or cycle time is the speed at which a swimmer strokes—strokes/minute is the standard unit. The methodology for finding stroke rate is similar to finding distance per stroke and may be found knowing the distance underwater and the number of strokes per length. The distance underwater, or in this case what is more important is the time before the first stroke event which can be subtracted from the total time for the length to give the total time spent stroking that length. The stroke rate is then found by dividing the number of strokes in the length divided by the amount of time spent stroking and then converting it to a familiar format such as strokes/minute. A more precise stroke rate may be found by using the exact time stamps of all of the stroke events over the course of the length. As the signals may be oscillatory signals, this reading is effectively the frequency of the signal. This higher resolution stroke rate may also be able to show a change in stroke rate across a length which may be useful information to show if a swimmer is speeding up over a length or if they are simply putting in more effort to gain the same output speed and becoming inefficient.

Swim Metrics: Cadence

Cadence is a measure of a swimmers stroke rate for their left arm vs their stroke rate for their right arm. This metric is only used in freestyle and backstroke where both arms move independently. This is simply measured using the techniques for stroke rate until the time stamps for each stroke event are determined. Then the time difference from the left stroke to the right stroke is compared against the right stroke to left stroke and may be displayed in various ways such as a ratio. If a swimmer is swimming evenly with a perfectly steady stroke cadence then this will be equal to 1. If the swimmer is not swimming evenly, also known as "galloping", then this will be a number other than 1.

Swim Metrics: Breathing Pattern

Breathing pattern is the number of breaths a swimmer takes per length and in a stroke such as freestyle can also be a pattern of how many times a swimmer breathes to the left and to the right sides of their body. The number of breaths per length and breathing pattern for each stroke may be calculated based on the motion of the swimmers head moving through the water seen in the signal from the sensors on the device 21 or from derived values profiles such as the swimmers pitch, yaw, and roll measurements. In freestyle the swimmer's head rolls either to the left or the right passing a certain point which places their mouth out of the water and allows for a breath. Breathing in backstroke is not important as the swimmer can constantly breathe with their head out of the water. Breathing for breaststroke is simple as the swimmer breathes every stroke, so each stroke equals one breath. Butterfly breathing may be measured by the change in pitch as the swimmer keeps their head down and in the water when they do not breath, but they raise their head and in turn pitch when the take a breath as they need to bring their mouth above the water. There are special cases in butterfly where the swimmer either breathes every stroke (seen as a single peak level over the length) or breaths to the side (seen and calculated in another axis). Also mentioned previously, these limits may be automatically adjusted as the unit learns the swimmer's specific technique.

Swim Metrics: Breaths Per Length

Breaths per Length is the number of the total breaths-per-length as an addition of all of the breaths taken in a single length calculated above.

Swim Metrics: Swimmer Speed

The swimmer's speed may be found in multiple methods. An average speed over the length may be found by simply dividing the length of the pool by the time taken to swim the length. A more accurate or higher resolution speed may be found using methods discussed later in this section (the Linear Velocity section) by integrating the accelerometer data to gain real time velocity profile of a swimmer over the course of the length.

Swim Metrics: Swimmer Position

The swimmer's position is the sum of the swimmer's relative positions in the direction of the pool. This relative position is determined using the methodology discussed later in this section by integrating the calculated velocity values. The position is reset each length of the pool when the swimmer touches the wall.

Swim Metrics: Heart Rate

The heart rate is calculated directly from a heart rate sensor that is either clipped on the swimmer's ear or resting against the swimmer's temple. The sensor returns a signal which is filtered and processed to determine each peak of the signal, or pulse. This pulse is then correlated to the standard beats per minute value by determining the time between each pulse.

Swim Metrics: Horizontal Drift

Horizontal drift may be measured using the approximate change in the horizontal position of the swimmer as the swimmer moves down each length. The relative position calculations are done using the integration techniques mentioned later in this document using the accelerometer readings. In this case, the accelerometer readings being integrated may be the axis perpendicular to the lane. This metric is more meaningful when a swimmer is alone in a lane to see how much they naturally drift as they swim which is an important measure of inefficiency.

Swim Metrics: Turn Time

Turn time may be determined by a calculation of the time from when the swimmer began their turn to when they push off the wall. As discussed in the Split Times section, the turn events have a distinct signal which can be broken down into a start of turn event and an end of turn event. The turn time is then calculated as the end of turn time minus the start of turn time.

Swim Metrics: Calories Burned

Calories burned may be calculated based on the swimmer's heart rate with respect to time, combined with the swimmer's age, weight, and size. This metric may be quite accurate as the swimmer's live heart rate is recorded with respect to time compared to most heart rate-calorie calculations which simply use a total average heart rate and workout time.

Swim Metrics: Lactic Acid Levels

Lactic acid levels are an important measurement to a swimmer and coach but most existing techniques are invasive and requires the athlete to stop in the middle of their workout to take a reading. Live lactic acid levels may be approximated using the key metrics measured with the WSU 12. Some known variables need to be input to make this approximation possible. These variables may include some or all of the swimmers lactate threshold, lung capacity, age, weight, and size. The calculated live heart rate allows for the amount of time spent above the swimmers lactate threshold as well as magnitude to be calculated. Combining this, the swimmers stroke rate, and number of breaths per length, the swimmers lactic acid levels or content can be calculated.

Swim Metrics: Kick Rate

When a swimmer is kicking in a kick set, the speed at which they are kicking, or their kick rate, may be determined. Similar to each swim style, each kick type may have its own unique signal profile from the sensors. These signals are also oscillatory in nature and can be analyzed similarly to how the swimmers stroke rate is calculated. The kick rate is effectively the frequency of the oscillatory kick signal measured by the sensors after the break out event. This calculation also allows for the number of kicks taken in a given length to be calculated similarly to how the swimmer stroke count can be calculated. Kick sets could also be included in an initial calibration.

Swim Metrics: GPS Tracking

This functionality may be mostly beneficial for triathletes or open water swimmers and may be used to track their swims in open water to provide them with velocity and position data which may no longer be available from the accelerometer as they are not in the fixed pool system. Units with this GPS capability could even be used for an entire triathlon by designing the unit to sense when the athlete transitions to biking and then running. It could be used to sense all of the swimming functionality and then go on to sense biking and running speed, GPS tracking, steps taken, and all biometric information from the HR monitor.

Swim Metrics: Swim Time, Rest Time, Workout Time

During the swimmers workout there is a timer constantly running. This timer allows for the entire workout time to be calculated as the last end swim event minus the first start swim event. This timer also allows for split times and swim times to be calculated. When every swim time in a given workout is summed up, the total swim time of a workout can be calculated. The total time spent at rest can also be calculated by the total workout time minus the total time spent swimming.

Swim Metrics: Distance Swam

As the pool length is a known or input variable, the distance swam in a given workout is easily calculated by the total number of lengths swam in a given workout multiplied by the length of the pool.

Pitch, Yaw, Roll

Data obtained from the gyroscope (or other sensors) on the wearable swimming unit may be used by the system 10 to calculate the swimmer's angular velocities about a plurality of axes. For example, by integrating this raw sensor data using numerical methods such as the Euler Method described below, the angular position for each axis (e.g. pitch, yaw and roll) can be determined. The pitch, yaw, and roll of the swimmer's head may be beneficial in determining many of the swim metrics and may be described in further detail below.

The Euler Method includes calculation of two successive derivatives (accelerations) at times t and t+dt. This provides the velocity at t+2*dt. Position is found in the same way but using two velocities in order to gain the change in position over that interval.

In a sample, non-limiting example, the following steps may be illustrative in describing how integration of gyroscope data may be used to obtain quaternions:
1) Calculate the time interval for calculations;
2) Calculate the magnitude of the input vector for integration and then invert that vector;
3) Calculate the cosine and sine terms used to find the quaternions; and
4) Calculate the 4 new quaternion values using a forward Euler Method combining the previous 4 quaternion values as well as the newly calculated cosine and sine terms.

The steps are merely provided for illustrative purposes, variations of the steps, omission or substitution of various steps, or additional steps may also be considered.

An approximation may be used whereby the rotation rates do not change during the integration step time. By applying this approximation, the non-linear ordinary differential equation (ODE) may be replaced with a linear-ODE. The equations may then be used to calculate the quaternion at the new time, given the quaternion at the old time, and the gyroscope rotation rates.

A potential benefit is that the number of divisions is minimized to one: when calculating the inverse square term. In other situations where division would normally occur, the multiplication of the inverse square term is applied instead. The reduction of the number of divisions may potentially be beneficial through reducing computational time, which may be potentially useful, especially for the AVR architecture, which doesn't have a floating point unit (FPU).

Linear Velocity

In a sample, non-limiting example, the following steps may be illustrative in describing how integration of accelerometer data may be used to obtain velocity:
1) Find the current forces on the unit body;
2) Set the gravity correction (using gravity correction method described later) vector based on the frame set by the body forces;
3) Determine the time step between calculations; and
4) Compute the velocity in each direction using a simple Euler discrete integration.

The steps are merely provided for illustrative purposes, variations of the steps, omission or substitution of various steps, or additional steps may also be considered.

The accelerometer sensor on the wearable swimming unit may calculate or measure data used by the WSU 12, hub, or other computing device to calculate the linear acceleration in each of the x, y, and z directions. Firstly, this data may need processing in order to remove the effects of gravity on the sensor readings as acceleration due to gravity may render inaccuracies in any data calculated based on this raw sensor data. Once readings due to gravity are removed, the offset data could then be integrated using similar numerical methods such as the Euler Method described above in order to obtain the unit's relative linear velocity in each direction. The linear velocity in each axis could then be integrated using similar numerical methods in order to obtain the unit's relative position in each axis.

The body forces are sensed by the accelerometers and may be converted from the body-fixed frame "b" to the inertial frame "i" by multiplying by the direction cosine matrix R_ib, which may be calculated from the orientation quaternion. This vector may then be added to the gravity vector in the inertial frame, which may be a constant (0,0,−g) vector.

From the equation "acceleration=body_forces+gravity", the translational acceleration in the inertial frame may be calculated.

While it may be possible to obtain relative position and velocity of the WSU 12 from raw accelerometer values, challenges may be faced in many real life applications due to an exponential buildup of error. The accelerometer sensor produces analog measurements which may need to be converted to digital values in order to be read by a computer using an analog-to-digital converter (ADC). This conversion creates the first error phase which may be due to the fact that the ADC cannot infinitely sample the analog signal which results in a sampling error. The next phase of error may be caused by numerical methods which generate error by their nature as they are simplifications of complex mathematical functions which allow computers to approximate the results of these functions. Therefore, the next phase of error occurs when using numerical methods to remove the effects of gravity from the raw accelerometer data. The next phase of error is within the first integration to get the linear velocity in each axis. The final error phase is in the second integration which integrates the linear velocity to gain linear position. To get to these relative position readings, three levels of error have now been used to calculate new data which can render the results virtually useless. For example, there may be three integrations in a row, each of which may compound the numerical integration error. The three integrations may include: (1) integrating gyroscope data to determine angles needed to eliminate gravity from accelerometer; (2) integrating acceleration to determine velocity; and (3) integrating velocity to determine position.

Error Correction

In order to address this error and correct for it, an application specific system may be modeled in order to provide boundaries to correct for the error and minimize "drift". Swimming is a good sport for this kind of modeling because boundaries can be placed on position as the pool is a fixed length (25 yards, 25 meters, or 50 meters). This fixed length allows the position error to be offset every pool length in order to minimize drift. Velocity error can also be corrected as there are natural limits on how fast a swimmer can swim (e.g. between 0 and 4 m/s) and the swimmer hits a 0 velocity in the direction of the pool every length as they are changing directions during a turn. Velocity drift can be further minimized as each unit is used more by the swimmer who owns it as the unit may begin to learn on average how fast its swimmer can swim for each stroke and how fast they generally swim compared to their various metrics such as stroke rate and distance per stroke. On top of that, the unit may use historical data or even the previous lap's velocity as another boundary, by using the distance of the pool divided by the swimmer's previous lap time (e.g. 25 m/12.5 sec~2.0 m/s average velocity). These important system boundaries allow control theory to be used and techniques such as a feedback loop in order to continuously correct for error build up in the system. Further error correction is done with the use of advanced predictive filter techniques such as a Kalman filter. The Kalman filter may be used to correct the error buildup and drift by first estimating or predicting a future state and then update the estimation using the measured values and then update the estimation technique to make it more precise based on the measured error. This iterative process eventually results in an effective filter technique which adapts as the system changes and ultimately results in reduced drift and error buildup over time. Further error correction could be done using the magnetometer readings as they provide an accurate heading with which the gravity vector could be corrected with which may decrease error in that phase of the system.

The feedback and additional accelerometer error correction functions may be implemented together within an "inertial navigation" method as shown below. The PID method, similar to the accelerometer error correction, assumes that the system is not undergoing strong accelerations. Thus, the body forces sensed by the accelerometer are due mostly to gravity, and are pointing along the Z axis. This Z axis may be converted from the body-fixed frame to the inertial frame using quaternions or by multiplying by R_ib, similar to the method used in the gravity removal. The body forces in the inertial frame are found, and under small accelerations these body forces should point along (0,0,1).

As the orientation drifts, the transformation from the body-fixed frame to the inertial frame may shift, and the body forces may not point along (0,0,1), but there may be a small error term. This is the z_error vector. This error is integrated and then the proportional and integral terms are added to the rotation rates, omega. This implementation may potentially be effective at correcting the roll and pitch errors, but may not be able to correct for yaw errors, as there is a rotational degeneracy about the (0,0,1) axis. This degeneracy may be corrected using a magnetometer to correct the drift in the yaw.

However, the degeneracy may not be critical as the yaw may be found to not be particularly important in most swimming applications.

A potential improvement to this method could be to adjust the weight of the error correction based on the magnitude of the acceleration.

Further accelerometer error correction may be conducted by applying an inertial navigation method, which may be comprised of the following steps:

1) Read sensor values from the accelerometer;
2) Run a simple integral controller to handle accelerometer bias drift;
3) Assume that over time the acceleration should be close to zero, and use the acceleration in the inertial frame as a feedback;
4) Transmit a signal to adjust the bias of the accelerometer. Use a low integration scaling factor to allow high-speed acceleration to get through;
5) Run a simple PID controller for drift correction;
6) Determine the direction of the gravity vector, using the accelerometer. The body forces should be pointing along +Z;

7) Determine the direction of +Z in the body frame using quaternions;
8) Integrate the error;
9) Add the error feedback to the gyroscope signal;
10) Integrate the orientation quaternion using the gyroscope data;
11) Integrate the velocity vector using the accelerometer data and the orientation quaternion; and
12) Reset the previous time step.

The steps are merely provided for illustrative purposes, variations of the steps, omission or substitution of various steps, or additional steps may also be considered.

In some embodiments, the acceleration of the swimmer may be assumed to be approximately zero over time.

This bias integral may be the acceleration in the inertial frame integrated with a low multiplicative constant, which may potentially prevent it from accumulating too quickly, and may works to remove the constant bias of the accelerometer.

Under periods of high acceleration, the integration factor could be made to depend on the magnitude of the acceleration. For example, when the magnitude of acceleration is close to 1G, the weight of the integral may be set at a higher value, but as it departs from 1G, the weight of the integral may be set at a lower value.

Swim Metrics: Stroke Profile

The swimmers stroke profile based on the motion from the back of their head may be calculated and displayed either by the raw sensor data over time as they swim, or the pitch, yaw, and roll over time. This profile provides a good visual aid to judge their position through the water and can be used as a comparison over time to see how their stroke changes or can be compared against other athletes strokes or an optimal stroke profile to show where they have weaknesses. This stroke profile may be overlaid on top of the a video of the swimmer with the time stamps of the video and the time stamps of the data synchronized so that the swimmer and coach can use both the profile and the video to determine where they have flaws.

Swim Metrics: Velocity Profile & Power Cycle

Similar to the swimmers stroke profile, the swimmer linear velocity may be displayed over time to show a visual representation of how the swimmers velocity changes throughout the length. When this velocity profile is overlaid on a video with the time stamps synchronized, the profile and the video can be used together in order to show exactly where in the swimmers stroke that they are slowing down. This concept is effectively showing the swimmers power cycle as the video could be slowed down to show exactly when and where in the swimmers stroke that they are slowing down and becoming inefficient. This tool may allow coaches and athletes to target specific areas in the swimmers stroke which they need to address to become more efficient and effective swimmers.

Swim Metrics: Technical Efficiency

The WSU 12 may be able to compare the swimmer's specific technique against an "optimal" technique or an elite athlete's technique and provide them with a rating compared to them. This may allow the swimmer to compare themselves against known techniques of the top swimmers in the world. This technical efficiency score may be calculated using the key parameters measured for each stroke the swimmer swims and compared against those of an elite athlete. An optimal technique could also be defined based on the data from large numbers of elite athletes and combining their best traits into an optimized and smooth profile and set of parameters. This would provide a more unbiased rating as even elite athletes have flaws in their strokes that might give someone a high score simply because they mimic those traits. Technical efficiency can be rated against many things including metrics histograms which show the swimmers average performance metrics at different speeds for each stroke. This histogram or array of averages would provide an easy way to compare or rank different athletes based on running averages of performance metrics calculated in all of their workouts.

Live Feedback to Mobile Application

Each WSU 12 may wirelessly communicate with the individual or with the coach either directly or through a wireless hub. Wireless communication may come from the RF unit built in to the WSU 12 which could also have an external antenna built into the unit or strap in order to address potential challenges with transmitting when the unit is partially submerged, such as backstroke.

Figure 12:
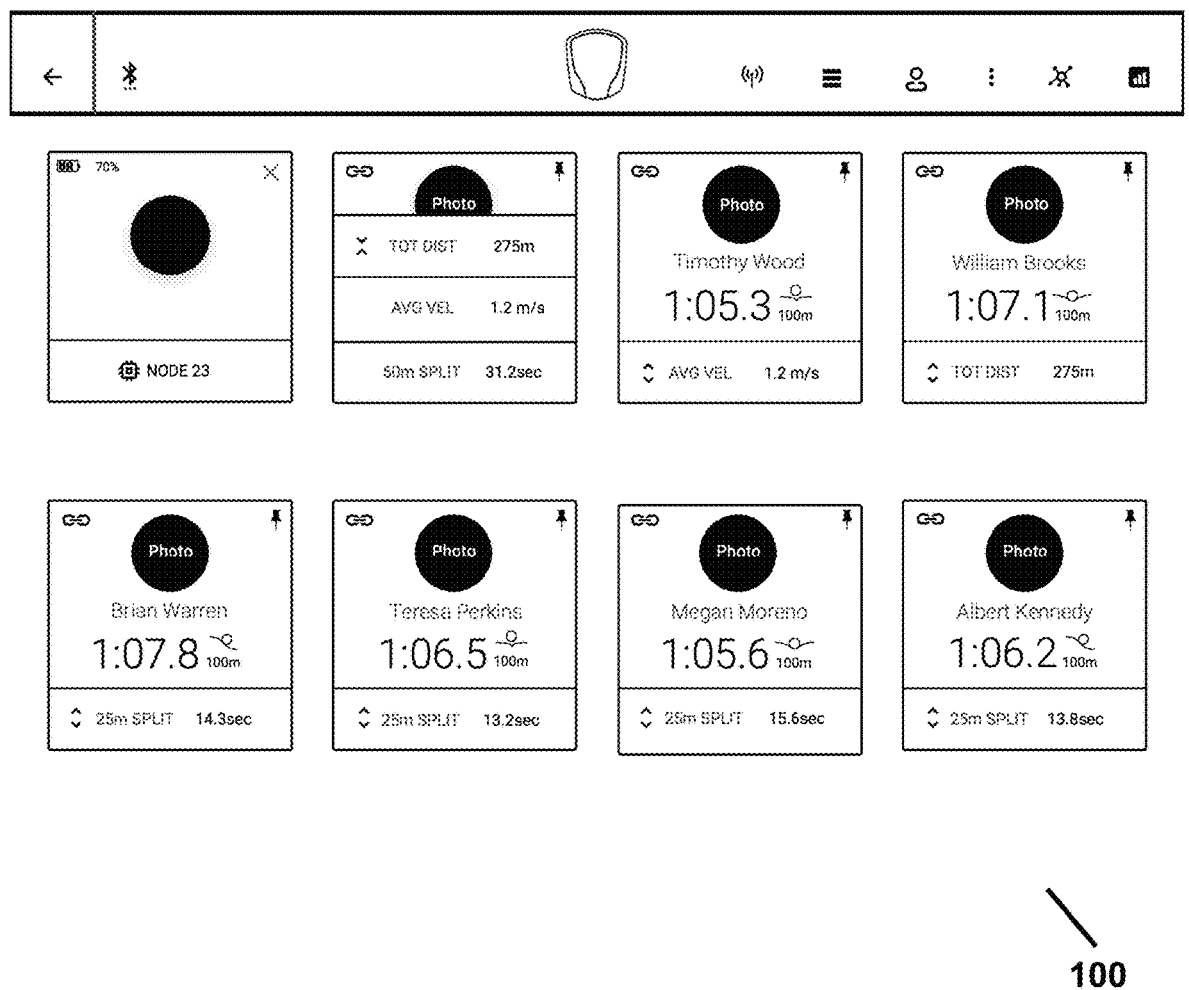
FIGS. 12 to 14 illustrate interfaces for an exemplary screen view of a user view of a mobile application according to some embodiments.
Figure 13:
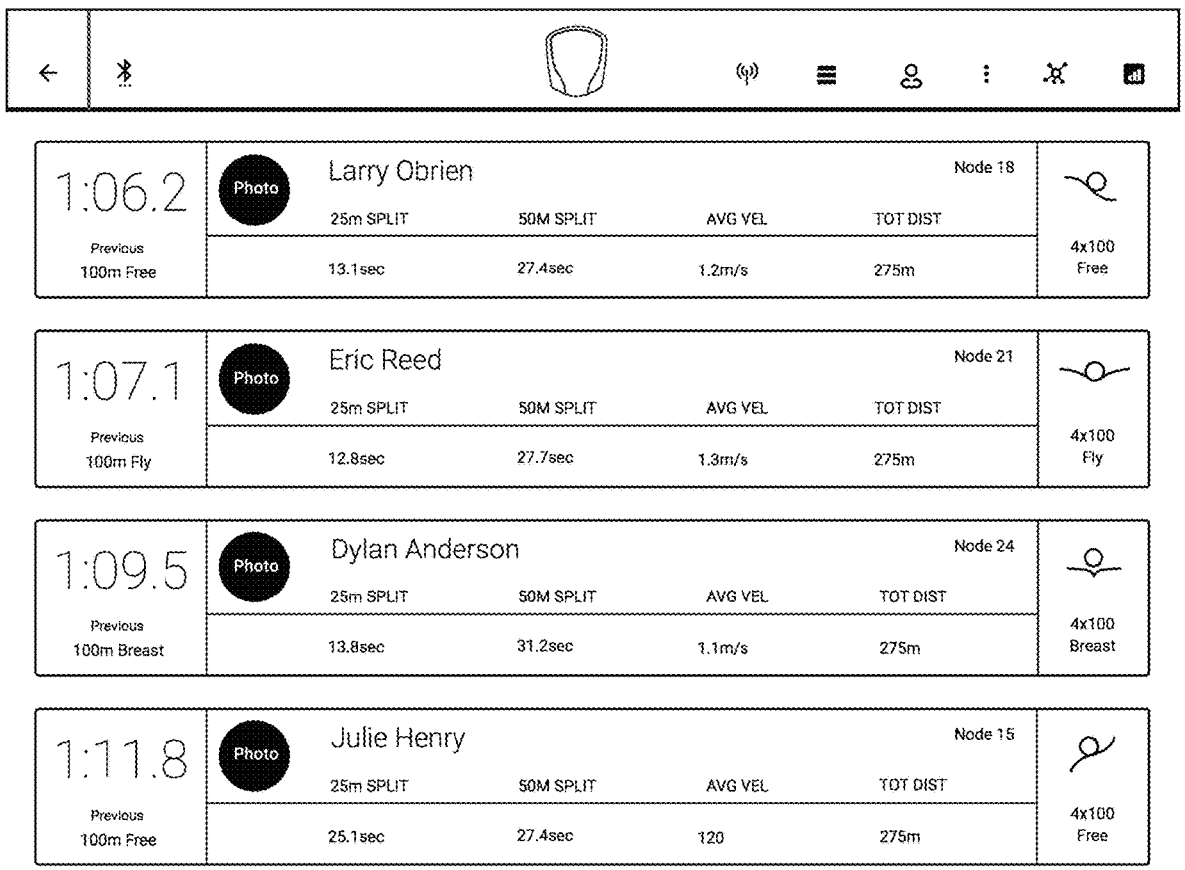
Figure 14:
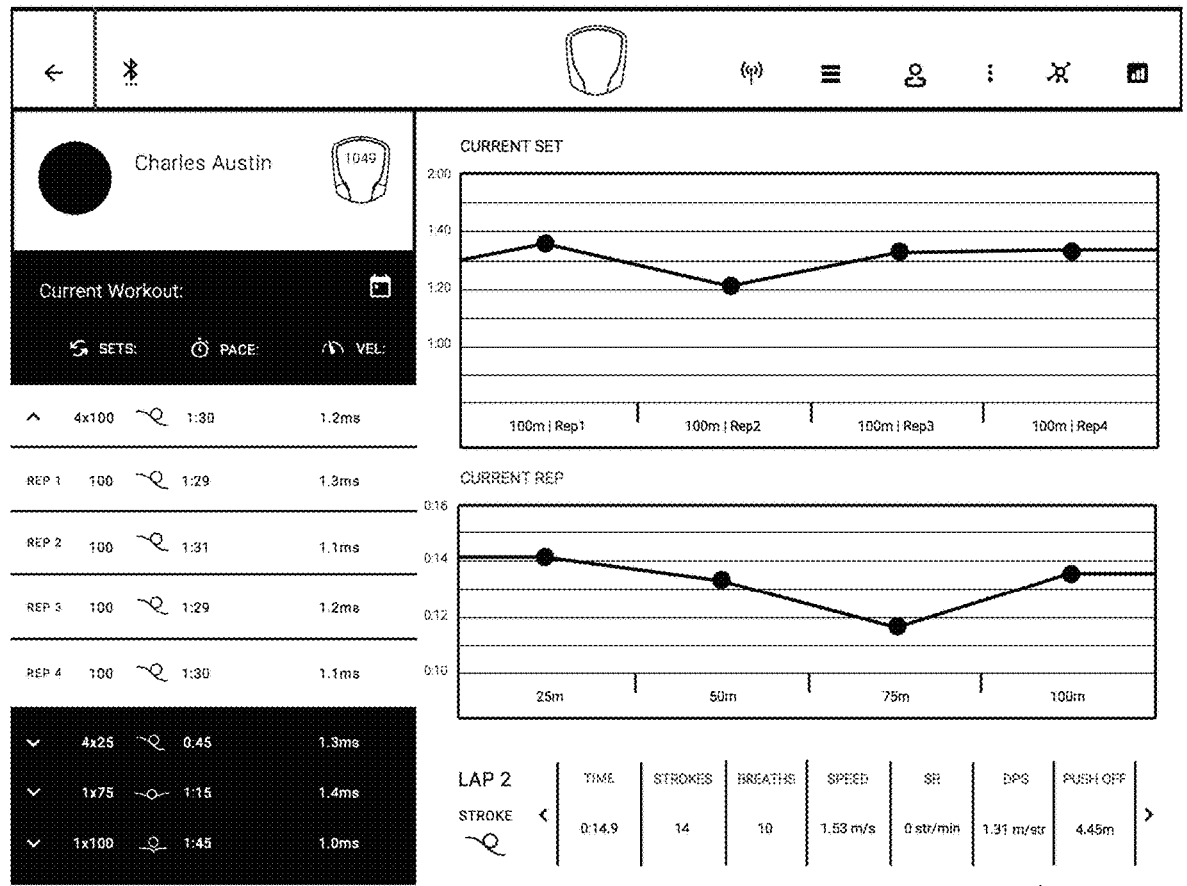

The data sent to the coach may appear on a mobile application on a device 12 showing each desired swim metric for each desired swimmer as shown in tile version example interface 100 of the team view in FIG. 12. The data may displayed in many ways including an interface 102 with a list view (as seen in FIG. 13), an interface 100 with a tile view (as seen in FIG. 12), or any other view. The coach or user may be able to filter which metrics they may like to see to allow them to minimize the amount of information being displayed if so desired. If the coach or user may like to see trends of a given swimmer, they may click on that swimmer to go into a more detailed swimmer view which may show the swimmers progression over the course of a workout. This may also show swimmers progression visually in graphs as shown in the interface 104 of FIG. 14. The interface 102 shown in FIG. 13 only shows a few metrics which may be chosen by the coach based on their customizable preference for a given workout. For example, some coaches may only want to see the live splits and heart rate of their swimmers for a given workout. On top of this, the application may allow the coach to video record a swimmer at any time using the video capability of the mobile device. The video may be synchronized with the time of the workout and the coach may tag the swimmer so that their specific metrics may be synced in time with the video for review either immediately or later online if they wish to upload it with the workout data.

While the application 16 screen image (e.g. interfaces 100, 102, 104) shows the mobile application 16 in use by a coach, the application 16 could also be used by an individual swimmer. The individual may connect their swimming device to the application and could place their mobile device on deck in their lane. A water resistant stand or suction cup mount could be provided to make this more practical. This may allow the swimmer to see their planned workout, their progress through the workout, and their live performance metrics as they swim. It may also have the option to record them as they swim as most mobile devices are equipped with front cameras. This may allow the swimmer to review exactly how they are swimming. The mobile device 16 could alternatively stream the application screen onto an external display such as a TV or projector. This would allow for swimmers and/or coaches to view their data from a distance.

Live Feedback to Swimmer

In various possible non-limiting implementations of example embodiments, the swimming unit (WSU 12) may also contain audio feedback for the swimmer either in the form of a standard in ear headphone or in the form of a bone conduction headphone as shown in FIGS. 10 and 11. The audio feedback may be used as one-way communication from the coach to the swimmer. The audio feedback could also be set to automatically read out desired metrics to the swimmer as well as to provide technique feedback based on measured performance and efficiency which is explained in this document. Specific metrics may be chosen to be read out to the swimmer either by selecting the desired metrics on the mobile application or on the unit itself. For example, the swimmer may want to always hear their 50 m splits during their workout so the unit may call out that time. For example, "32.1" may be said through the ear piece as: "thirty two point one".

Figure 15:
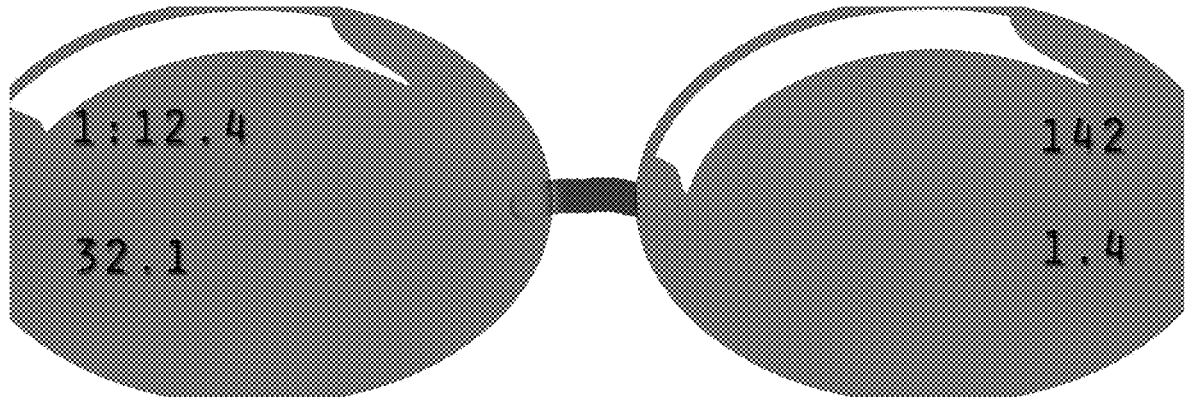
FIG. 15 illustrates an implementation of an in-goggles display of the wearable swimming unit device according to some embodiments.
Figure 16:
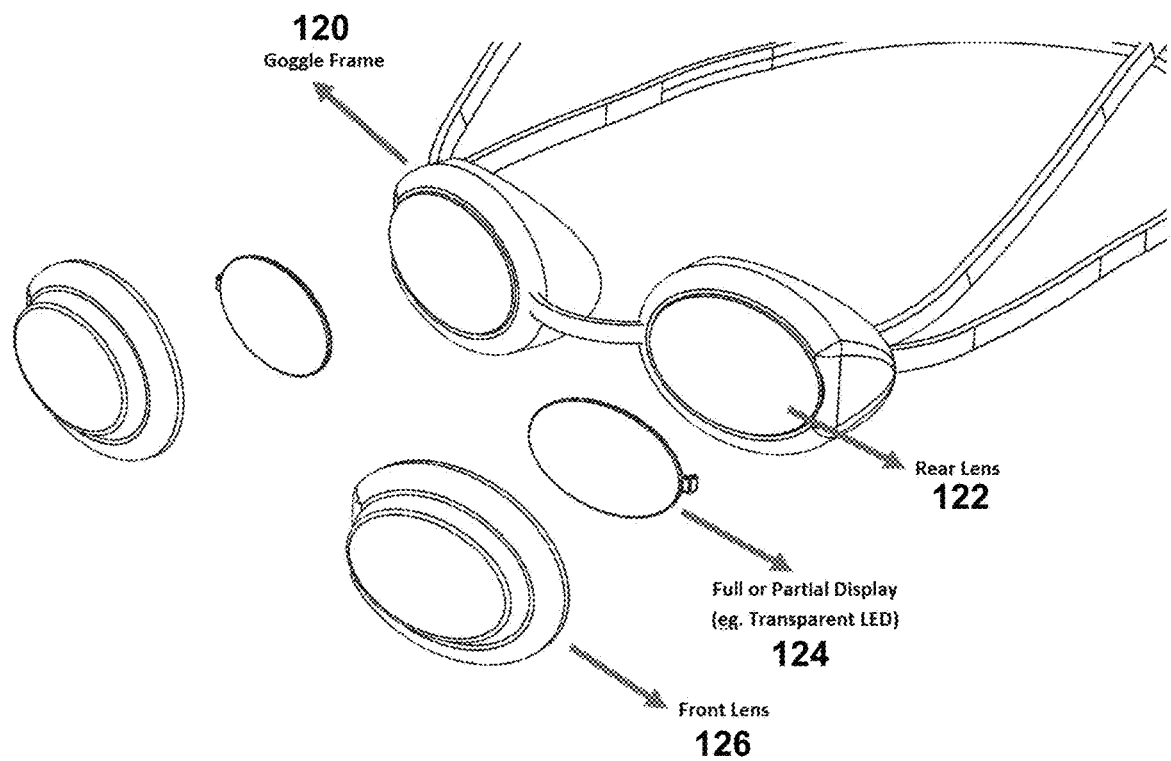
FIG. 16 illustrates an exploded view of a goggle portion of an implementation of the wearable swimming unit device according to some embodiments.

The swimmer unit could also contain a heads-up display (HUD) which may provide visual feedback for the swimmer showing desired swim metrics and information within the swimmer's goggles as shown in example interface 106 of FIG. 15. FIG. 15 shows the HUD showing the most important metrics such as heart rate in the top right, distance per stroke in the bottom right, total swim time in the top left, and the previous 50 m split in the bottom left. The HUD could either be done using a small screen within the goggle combined with a magnifying glass, through the use of a high resolution transparent screen such as transparent LED technology, or through any other technology. The transparent screen may be clear as a standard goggle, but may display key swim metrics in certain locations of the goggle. The transparent LED HUD concept is and how it could be assembled is shown in FIG. 16. HUD device may have a goggle frame 120, a rear lens 122, a transparent LED screen 124, and a front lens 126.

Figure 17:
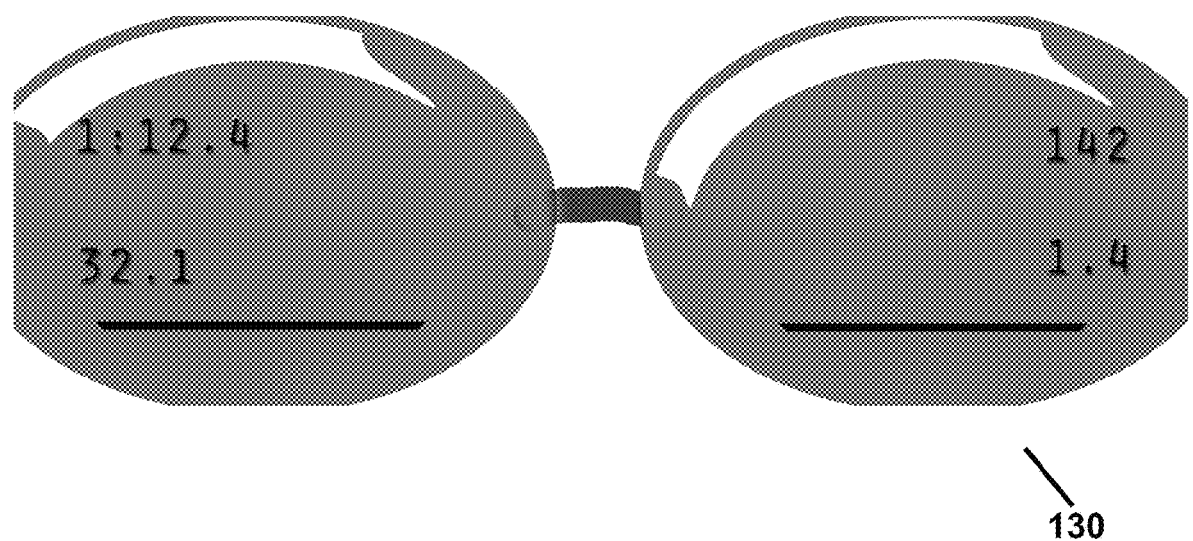
FIG. 17 illustrates an implementation of an in-goggles display of the wearable swimming unit device according to some embodiments.
Figure 18:
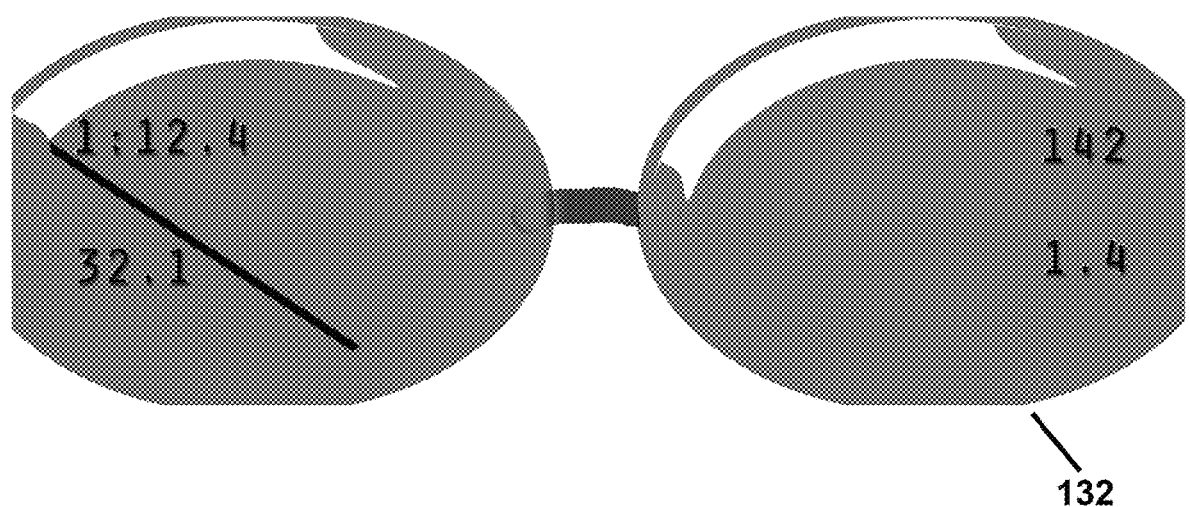
FIG. 18 illustrates an implementation of an in-goggles display of the wearable swimming unit according to some embodiments.

This transparent screen HUD in the goggle could also be used as a pacing system. The swimmer could enter a goal time into the mobile application and choose the pacing system option which may provide a line in the goggle which may appear to be on the bottom of the pool to the swimmer and may move at the desired goal pace as shown in the interface 130 of FIG. 17. This behaves similarly to the line shown on television showing world record paces ahead of the swimmers as they race. The line may stay level with the bottom of the pool by using the pitch, yaw, and roll values as the swimmer moves their head during the swim as shown in the interface 132 of FIG. 18. The line may "move" further down the pool from the perspective of the swimmer if they were slower than the pace and may "move" behind the swimmer if they were faster than the pace. This is similar as to how fighter pilots' helmets work by showing them the horizon at all times regardless of their rapid motion changes.

It is possible that the swimmer may want to use the swimming unit during official competitions when live feedback may likely be frowned upon. To address this, a competition version or mode could be implemented to turn off all feedback.

It is also possible for the metrics from the device to communicate to another device such as a smart watch to provide visual feedback as the swimmer swims. The WSU 12 may also be equipped with a vibration motor to provide haptic feedback to the athlete as a buzzer from coach to gain the swimmers attention or as a specific signal defined by the coach or athlete (e.g. a pacing buzzer, or warning for any metric goal).

Auto-Coaching

The swimmer unit may implement processes and operations that use the multiple swim metrics and their trends in order to determine inefficiencies in the swimmer's technique and can provide tips to the swimmer if desired to help them address those inefficiencies. The tips may be automatically and dynamically generated. The auto-coach functionality may offer live technical feedback to the swimmer based on changes in their efficiency or in comparison to a more "optimal" swimmer. These tips can either be in an audio or visual form. This functionality may be mainly aimed at individual swimmers that do not have a coach.

Coaches continued use of the data may provide information of exactly how coaches interact with the data for their athletes and how they react to negative trends. This can be translated into automatic recommendations for a solo swimmer to modify their training regime based on a large database of coach's reactions to similar trends. These recommendations may even be able to outline average success rate of the recommendations.

More recommendations can be provided based on the swimmers deviation away from their running averages for each metric (e.g. averages such as the histogram of metrics at different speeds concept).

Auto-coaching may note inefficiencies compared to the swimmer's previous swimming patterns by using their measured metrics over time. The unit could automatically determine if the swimmer is slowing down and correlate that to changes in their other metrics. For example, if the swimmer slows down and their heart rate and stroke count also slow down, then they are likely purposely slowing down and no advice may be given. If the swimmer slows down and their heart rate and stroke count increase, then the unit may determine that the swimmer is becoming inefficient and could tell the swimmer "increase efficiency by lengthening strokes". Another example may be if the unit sensed the swimmer's stroke rate increasing but speed remaining the same and the unit could tell the swimmer the same advice of lengthening strokes as the increased stroke rate is inefficient since it is not increasing speed. The auto-coach could also provide other basic tips such as not breathing into or out of the wall, alternate their breathing pattern, if the swimmer is drifting in the lane, if the swimmer approaches their max heart rate, etc.

Media Player

The WSU 12 may include local memory or a removable memory card which may be used to store music which the swimmer could listen to through the audio headphone. The wearable swimming unit may have buttons for standard control of the music as mentioned herein and as seen in FIG. 10. The music function could be used with or without a coach, but the coach may have the ability to disable the music function if desired. When the auto-coach functionality is in use by the swimmer, the music function may also be available, but the music may fade out when the auto-coach tips are being read to the swimmer and then the music may fade back in when complete.

Workout Building

The swimmer unit may sense the different swimming strokes, kick, pull, and drill as well as the distance of each swim repetition. The unit may then be able to find patterns within the workout in order to group similar repetitions into sets. This may build the workout into a form similar to how a swimmer is accustomed to reading it. This functionality is especially useful for solo swimmers who may like to keep track of exactly how far they swam and in what capacity as they may not necessarily have a planned workout in advance as a coached team may. However, the swimmer may be able to build a workout on their online profiles before the workout and this workout building functionality of the WSU 12 may allow the swimmer to automatically follow along a workout as the unit may sense when they have completed a set and could even read out the next set through the audio feedback. If the coach or athlete plans builds the workout in advance and uploads it onto the application, then the planned workout can be used for further error correction since the units would know in advance what the swimmer was supposed to swim in terms of distance, stroke type, and pace time.

Online Profiles for Performance Tracking & Swimmer Social Network

Figure 19:
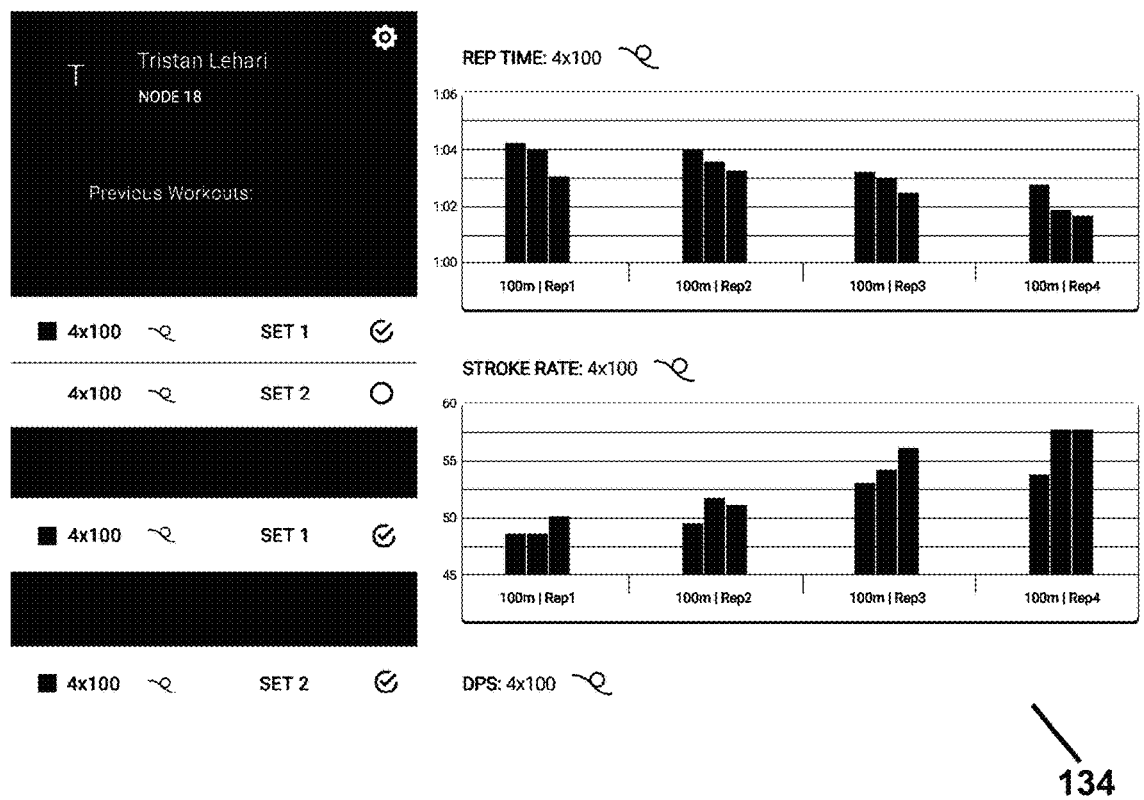
FIG. 19 illustrates an interface for an exemplary screen view according to some embodiments.

At the end of the workout the "built workouts" may be linked to each swimmer's unique ID and may be uploaded onto an online database once the mobile device is connected to the internet again as mentioned earlier. This database may be the backend of an online platform where each swimmer may have their own profile which may be set up upon purchase of the wearable swimming unit. These online profiles may be able to look up their workouts, performances, as well as historical trends similar to what is shown in the interface 134 FIG. 19. The coach may have access to the data for each of their teams' swimmers so that they could also review each swimmer's performance and trends. This data may be used in order to track how well a swimmer has been performing in practice as well as to see if certain styles of workouts directly result in better times in swim meets. Various analytical tools may be built and used by coaches and athletes in order to compare their performance and training over time. Coaches may also be able to flag poor performance or trends and comment within the web application for the swimmer to see.

The online platform may also be used as a social network for swimmers or directly linked to other social networking platforms in order to connect swimmers and provide a method of publishing their workouts as desired. Swimmers may be able to have "friends" connected to their profiles which may allow them to plan workouts together even if they do not live in the same country. This may also allow for online teams to be created where a group of solo swimmers could plan workouts with each other and effectively train together from a distance. This concept also works for existing teams where they may have access to their team page and plan workouts together as well as other team events. Swimmers may also be able to save their workouts and recommend them to others. These workouts may be publicly accessible and users may be able to rate them. This may create a swimming "Workout Bank" which individual swimmers could use to make their own workouts. Coaches may be able to block workouts they designed if they did not wish them to be publicly available.

Goal Setting

The online platform as well as the mobile application may allow swimmers and coaches to enter in a desired workout with desired goals for that workout. The units may track performance throughout the workout and may display or notify the coach and or the swimmer where they achieved and where they fell short of those goals. The units may be able to provide live feedback to the swimmer and tell them if they are starting to miss their goal times or other metrics. This is also where the pacing system could be used within the HUD for the swimmer to see a visual representation of their goal times and give them something to "chase".

Unit Competition & Gamification

These units may also be used as a way for swimmers to compete with each other, regardless of if they are on the same team. Two or more swimmers from around the world could plan a workout together, swim that workout whenever it is convenient for them, and then compare their results on the online platform. This allows swimmers from around the world to compete against each other or train with each other without needing to be in the same place. There could also be a leaderboard set up for each workout in the workout bank which may show all of the swimmers from around the world that have tried that workout and where they rank.

The units could also be used together if multiple people have them in the pool at the same time. The system may recognize other units/competitors in the pool and may allow you to challenge them and may determine the results live. This gamification of swimming may add a new element to solo-swimming to keep the swimmers having fun and entertained, while still trying to reach their goals. This may work better if the swimmer has their mobile device in their lane so they can see who else is "online" in the pool and challenge them or train together. They could be in the same lane and simply add an interval for leaving time in between each other.

Further Wearable Sensors

Similar sensor units could also be placed on or within the swimmer's bathing suits in order to gather further information and swim metrics such as kick rate, body angle, etc. The sensors on or within the bathing suits may be able to communicate with the swimmer unit on the swimmers head to gather even more data. These units may both integrate with the entire system and send the data live to the coach or a solo-swimmers mobile device. These sensors could even go beyond the swimmer's bathing suit, cap, and goggles to eventually become tape sensors for body parts to track entire swimmer motion in the water.

Embodiments may provide a method, performed by a wearable computing device 12 comprising a display, and at least one bio-signal measuring sensor, comprising: acquiring at least one bio-signal measurement from a user using the at least one bio-signal measuring sensor; processing the at least one bio-signal measurement in accordance with a profile associated with the user; determining a correspondence between the processed at least one bio-signal measurement and a predefined display control action; and in accordance with the correspondence determination, modifying an image displayed on the display. Optionally, the display may be part of the wearable computing device 12 itself, or it may be provided on a separate computing device that is connected to or otherwise in communication with the wearable computing device. The separate computing device may also be a wearable device worn by the user. The bio-signal measuring sensor is an example sensor. Other example sensors include accelerometers, gyroscopes, and so on.

In a particular aspect, a wearable computing device 12 is provided including a camera, a display, and bio-signal measuring means to sample a user's environment as well as the user's bio-signals, determining the user's state and context through sensors and user input.

In a particular aspect, the bio-signal measuring system may include at least one of (1) an electrical bio-signal sensor in electrical contact with the user's skin; (2) a capacitive bio-signal sensor in capacitive contact with the user's skin; (3) a blood flow sensor measuring properties of the user's blood flow; and (4) a wireless communication sensor placed sub-dermally underneath the user's skin.

In another aspect, the wearable computing device 12 may include at least one user-facing camera to track eye movement. In a particular aspect, the wearable computing device 12 may be in a form resembling eyeglasses wearable on the user's face. Optionally, at least one camera may be oriented to generally align with the user's field of view.

In another aspect, the wearable computing device 12 may be in a form of at least one sensor adapted to being placed at or adhered to the user's head or face. Each sensor may optionally communicate with one another either through wires or wirelessly. Each sensor may optionally communicate with a controller device either through wires or wirelessly. The controller device may be mounted to the wearable computing device 12 in order to reside at or near the user's head or face. Alternatively, the controller device may be located elsewhere on the user's body, such as in a bag or pocket of the user's clothing. The controller device may also be disposed somewhere outside the user's body. For example, the sensors may monitor the user, storing data in local storage mounted to the wearable computing device, and once moving into proximity with the controller device, the sensors, or a transmitter of the wearable computing device 12 may transmit stored data to the controller device for processing. In this implementation, the wearable computing device 12 may be predominantly usable by the user when located nearby the controller device.

Other Sports

The concepts and methodology listed in detail in this document may be applied directly to other sports. More specifically any race-based sport where there is a time or speed associated with the final result or outcome of the race. In all race-based sports, athletes have specific performance metrics that both they and their coaches keep track of throughout training and competition to gauge their performance effectiveness. In the vast majority of cases, these metrics are calculated manually with a stopwatch or simply estimated. In many sports there are also generally a large number of athletes with only one or two coaches which make it almost impossible to calculate all of the metrics for every athlete. Naturally since it is not possible to calculate all of the metrics, it is impossible or impractical to log the metrics for future review. That is where this technology comes into play. All race based sports could have a unit like the WSU 12 which would automatically calculate key performance metrics and/or biometrics on the athlete's body and transmit that in real time to a coach's tablet. A non-exhaustive list of potential sports includes American Football, Australian Football, Baseball, Biathlon, Canoeing, Cross Country Running, Cross Country Skiing, Downhill Skiing, Dressage, Endurance Riding, Eventing, Horse Racing/Steeplechase/Hurdles, Kayaking, Lacrosse, Marathon, Mountain Biking, Modern Pentathlon, Polo, Race Walking, Road Bike Racing, Rowing, Rugby, Sailing, Equestrian Show Jumping/Hunter, Sled Sports, Snowboarding, Soccer, Surfing, Track Cycling, Track Running/Hurdles, Triathlon, and Windsurfing. This non-exhaustive list of sports includes only outdoor sports as they would be simple transitions using the technology and methodology outlined in this document. Swimming is one of few indoor sports which is constrained enough (As discussed in the error correction section) to allow for these performance metrics to be accurately and consistently measured.

An adaptable unit may be created for all outdoor sports which calculates the athlete's position and velocity with a GPS module (which can have increased accuracy using sensor fusion techniques combining the accelerometer, gyro, and magnetometer) and calculates sports-specific metrics using sensors such as GPS, accelerometers, gyroscopes, magnetometers, biometrics sensors. Real-time feedback to a coach can be achieved with a GSM/3G module which would upload data directly to the cloud from the unit on the athlete and would be downloaded from the cloud by the coach's tablet. This removes the challenges of range in outdoor sports. This general unit may be placed in different locations on the athlete depending on the sport. For example, in equestrian sports the unit may be located on the horse to allow the unit to calculate important metrics such as the horses gait, jumping characteristics, and biometrics. In running and hurdle sports the unit may be placed on the athlete's ankle to calculate metrics such as gait, impact, biometrics, and jump characteristics. In cycling the unit may also be placed on the athlete's leg to calculate metrics such as rotation speeds and biometrics. In rowing or paddling sports the unit may be placed on the athlete's wrist to calculate metrics such as stroke rate, distance per stroke, and biometrics. These are just a few non-exhaustive examples from this non-exhaustive list of sports and is in no way limiting in the number of sports or specific metrics that could be calculated. This adaptable unit may contain similar or the same hardware for each sport, but may have a different external industrial design depending on the application to address the needs of that given sport (such as how it attaches to a body). The processes to convert raw sensor data into sport-specific performance metrics would change based on the application, but all of the methodologies to calculate those performance metrics would remain largely the same whether it be digital signal processing, filtering, sensor fusion, or machine learning techniques mentioned in this document.

The rest of the system would also include communication to the cloud and to the tablet from the cloud, the database, and the applications would have a different polish, graphics, and user interface as each sport requires.

Additional Technical Detail

It will be appreciated that any module or component exemplified herein that executes instructions may include or otherwise have access to computer readable media such as storage media, computer storage media, or data storage devices (removable and/or non-removable) such as, for example, magnetic disks, optical disks, tape, and other forms of computer readable media. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD), blue-ray disks, or other optical storage, magnetic cassettes, magnetic tape, magnetic disk storage or other magnetic storage devices, or any other medium which can be used to store the desired information and which can be accessed by an application, module, or both. Any such computer storage media may be part of the mobile device, tracking module, object tracking application, etc., or accessible or connectable thereto. Any application or module herein described may be implemented using computer readable/executable instructions that may be stored or otherwise held by such computer readable media.

Thus, alterations, modifications and variations can be effected to the particular embodiments by those of skill in the art without departing from the scope of this disclosure, which is defined solely by the claims appended hereto.

In further aspects, the disclosure provides systems, devices, methods, and computer programming products, including non-transient machine-readable instruction sets, for use in implementing such methods and enabling the functionality described previously.

Although the disclosure has been described and illustrated in exemplary forms with a certain degree of particularity, it is noted that the description and illustrations have been made by way of example only. Numerous changes in the details of construction and combination and arrangement of parts and steps may be made. Accordingly, such changes are intended to be included in the invention, the scope of which is defined by the claims.

Except to the extent explicitly stated or inherent within the processes described, including any optional steps or components thereof, no required order, sequence, or combination is intended or implied. As will be understood by those skilled in the relevant arts, with respect to both processes and any systems, devices, etc., described herein, a wide range of variations is possible, and even advantageous, in various circumstances.

What is claimed is:

1. A wearable computing device comprising:
    a movement sensor configured to generate sensor data output about at least one movement sensor axis;
    a processor coupled to the movement sensor; and
    a memory coupled to the processor and storing processor-executable instructions that, when executed, configure the processor to:
        retrieve sensor data output generated by the movement sensor, the sensor data output including acceleration data representing movement about at least one movement sensor axis associated with motion of a user head during a swimming stroke;
        determine data state estimations alterable in response to dynamically determined magnitudes of the acceleration data received successively over time;
        determine an oscillating signal profile by a plurality of successive data transformations of the acceleration data using the determined data state estimations for reducing data state estimation errors associated with the successive data transformations of the sensor data output;
        generate a performance metric based on the oscillating signal profile representing an oscillating pattern representing motion of the user head about the at least one movement sensor axis during the swimming stroke; and
        transmit, to an output device, an indication of the performance metric for providing substantial real-time feedback to a user during the swimming stroke.

2. The wearable computing device of claim 1, wherein the movement sensor includes a gyroscope, and wherein the sensor data output includes angular velocity data associated with motion of the user head during the swimming stroke.

3. The wearable computing device of claim 1, wherein the movement sensor includes at least one of a magnetometer or a barometer configured to reduce sensor data output error.

4. The wearable computing device of claim 1, comprising a goggle frame including the output device having a display for displaying in substantially real-time the indication of the performance metric during the swimming stroke.

5. The wearable computing device of claim 1, wherein the output device includes at least one of a bone conduction headphone or a waterproof headphone configured to output the indication of the performance metric to the user during the swimming stroke.

6. The wearable computing device of claim 1, wherein the output device is configured to transmit the indication of the performance metric to the user via haptic feedback.

7. The wearable computing device of claim 1, wherein the calculated performance metric includes at least one of stroke count, stroke rate, distance per stroke, swim time, stroke type, distance advanced underwater, push-off metric, cadence, breathing pattern, breaths per length, speed, position, heart rate, horizontal drift, turn time, rest time, or stroke type.

8. The wearable computing device of claim 1, comprising a communication transceiver coupled to the processor and configured to transmit the oscillating signal profile to an external computing device for classifying the oscillating signal profile based on a historical oscillating signal profile data set to identify swimming stroke type.

9. The wearable computing device of claim 1, comprising a communication transceiver coupled to the processor, and wherein the processor-readable instructions, when executed, configure the processor to:
    transmit, to an external computing device, the oscillating signal profile; and
    receive, from the external computing device, analysis data for presentation to the user during the swimming stroke, wherein the analysis data includes comparison data relative to other users within a given user class.

10. The wearable computing device of claim 1, comprising: a heart rate sensor coupled to the processor and configured to generate heart rate data based on data detected from at least one of an ear lobe or a temple of the user, and wherein the processor-executable instructions, when executed, configure the processor to:
    determine a heart rate of the user during the swimming stroke, and wherein the performance metric includes a heart rate metric.

11. A method of monitoring swim metrics by a wearable computing device, the wearable computing device including a movement sensor configured to generate sensor data output about at least one movement sensor axis, the method comprising:
    retrieving sensor data output generated by the movement sensor, the sensor data output including acceleration data representing movement about at least one movement sensor axis associated with motion of a user head during a swimming stroke;
    determining data state estimations alterable in response to dynamically determined magnitudes of the acceleration data received successively over time;
    determining an oscillating signal profile by a plurality of successive data transformations of the acceleration data using the determined data state estimations for reducing data state estimation errors associated with the successive data transformations of the sensor data output;
    generating a performance metric based on the oscillating signal profile representing an oscillating pattern representing motion of the user head about the at least one movement sensor axis during the swimming stroke; and
    transmitting, to an output device, an indication of the performance metric for providing substantial real-time feedback to a user during the swimming stroke.

12. The method of claim 11, wherein the movement sensor includes a gyroscope, and wherein the sensor data output includes angular velocity data associated with motion of the user head during the swimming stroke.

13. The method of claim 11, wherein the movement sensor includes at least one of a magnetometer or a barometer configured to reduce sensor data output error.

14. The method of claim 11, wherein the wearable computing device includes a goggle frame including the output device including a display, and wherein the method includes displaying in substantially real-time the indication of the performance metric during the swimming stroke.

15. The method of claim 11, wherein the wearable computing device includes at least one of a bone conduction headphone or a waterproof headphone, and wherein the method includes outputting the indication of the performance metric via acoustic waves via the bone conduction headphone or the waterproof headphone.

16. The method of claim 11, wherein the wearable computing device includes a haptic output device, and wherein the method includes transmitting the indication of the performance metric to the user via haptic feedback.

17. The method of claim 11, wherein the calculated performance metric includes at least one of stroke count, stroke rate, distance per stroke, swim time, stroke type, distance advanced underwater, push-off metric, cadence, breathing pattern, breaths per length, speed, position, heart rate, horizontal drift, turn time, rest time, or stroke type.

18. The method of claim 11, comprising: transmitting the oscillating signal profile to an external computing device for classifying the oscillating signal profile based on a historical oscillating signal profile data set to identify swimming stroke type.

19. The method of claim 11, comprising:
transmitting, to an external computing device, the oscillating signal profile; and
receiving, from the external computing device, analysis data for presentation to the user during the swimming stroke, wherein the analysis data includes comparison data relative to other users within a given user class.

20. A non-transitory computer readable medium storing machine interpretable instructions which, when executed, cause a processor to:
retrieve sensor data output generated by a movement sensor, the sensor data output including acceleration data representing movement about at least one movement sensor axis associated with motion of a user head during a swimming stroke;
determine data state estimations alterable in response to dynamically determined magnitudes of the acceleration data received successively over time;
determine an oscillating signal profile by a plurality of successive data transformations of the acceleration data using the determined data state estimations for reducing data state estimation errors associated with the series of successive data transformations of the sensor data output;
generate a performance metric based on the oscillating signal profile representing an oscillating pattern representing motion of the user head about the at least one movement sensor axis during the swimming stroke; and
transmit, to an output device, an indication of the performance metric for providing substantial real-time feedback to a user during the swimming stroke.

* * * * *